US010779792B2

(12) United States Patent
Arai et al.

(10) Patent No.: US 10,779,792 B2
(45) Date of Patent: Sep. 22, 2020

(54) MEDICAL X-RAY CT IMAGING APPARATUS, MEDICAL X-RAY RAY CT IMAGING CONDITION SETTING METHOD, AND NON-TRANSITORY COMPUTER READABLE MEDIUM

(71) Applicants: J. MORITA MANUFACTURING CORPORATION, Kyoto-shi, Kyoto (JP); NIHON UNIVERSITY, Chiyoda-ku, Tokyo (JP)

(72) Inventors: Yoshinori Arai, Tokyo (JP); Yoshito Sugihara, Kyoto (JP); Tomoyuki Sadakane, Kyoto (JP)

(73) Assignees: J. MORITA MANUFACTURING CORPORATION, Kyoto (JP); NIHON UNIVERSITY, Tokyo (JP)

( * ) Notice: Subject to any disclaimer, the term of this patent is extended or adjusted under 35 U.S.C. 154(b) by 0 days.

(21) Appl. No.: 16/171,366

(22) Filed: Oct. 26, 2018

(65) Prior Publication Data

US 2019/0125290 A1    May 2, 2019

(30) Foreign Application Priority Data

Oct. 27, 2017   (JP) .................. 2017-207855
Oct. 22, 2018   (JP) .................. 2018-198351

(51) Int. Cl.
*A61B 6/14*    (2006.01)
*A61B 6/00*    (2006.01)
*A61B 6/03*    (2006.01)

(52) U.S. Cl.
CPC .............. *A61B 6/544* (2013.01); *A61B 6/032* (2013.01); *A61B 6/14* (2013.01); *A61B 6/4085* (2013.01);

(Continued)

(58) Field of Classification Search
CPC ......... A61B 6/54; A61B 6/545; A61B 6/4085; A61B 6/544; A61B 6/467; A61B 6/46; A61B 8/461

See application file for complete search history.

(56) References Cited

U.S. PATENT DOCUMENTS

2005/0053190 A1    3/2005  Gohno
2010/0067650 A1    3/2010  Arai et al.
(Continued)

FOREIGN PATENT DOCUMENTS

| JP | 2005-080748 A | 3/2005 |
| JP | 2014-528284 A | 10/2014 |
| WO | 2013/049818 A1 | 4/2013 |

OTHER PUBLICATIONS

Search Report from the corresponding European Patent Application No. 18202747.4 dated Mar. 15, 2019.

*Primary Examiner* — David P Porta
*Assistant Examiner* — Fani Boosalis
(74) *Attorney, Agent, or Firm* — Shinjyu Global IP

(57) ABSTRACT

A medical X-ray CT imaging apparatus includes an X-ray generator that generates a cone beam, an X-ray detector, a support that supports the X-ray generator and the X-ray detector while the X-ray generator and the X-ray detector are opposed to each other, a turning drive unit that turns the X-ray generator and the X-ray detector, which are supported by the support, an imaging information receiving unit, and an X-ray output condition setting unit. The imaging information receiving unit receives an imaging area setting relating to at least one of a size of an imaging area, an imaging purpose, and an imaging region. The X-ray output condition setting unit automatically sets an output condition of the X-ray generator according to at least one of the size (Continued)

of the imaging area, the imaging purpose, and the imaging region, which are received by the imaging information receiving unit.

22 Claims, 18 Drawing Sheets

(52) U.S. Cl.
CPC ............ *A61B 6/4476* (2013.01); *A61B 6/469* (2013.01); *A61B 6/545* (2013.01)

(56) References Cited

U.S. PATENT DOCUMENTS

| | | |
|---|---|---|
| 2011/0044520 A1 | 2/2011 | Nakai et al. |
| 2014/0205066 A1 | 7/2014 | Kitagawa et al. |
| 2014/0270053 A1 | 9/2014 | Larson |
| 2015/0063536 A1* | 3/2015 | Kobayashi ............ A61B 6/032 378/20 |

* cited by examiner

F I G. 6
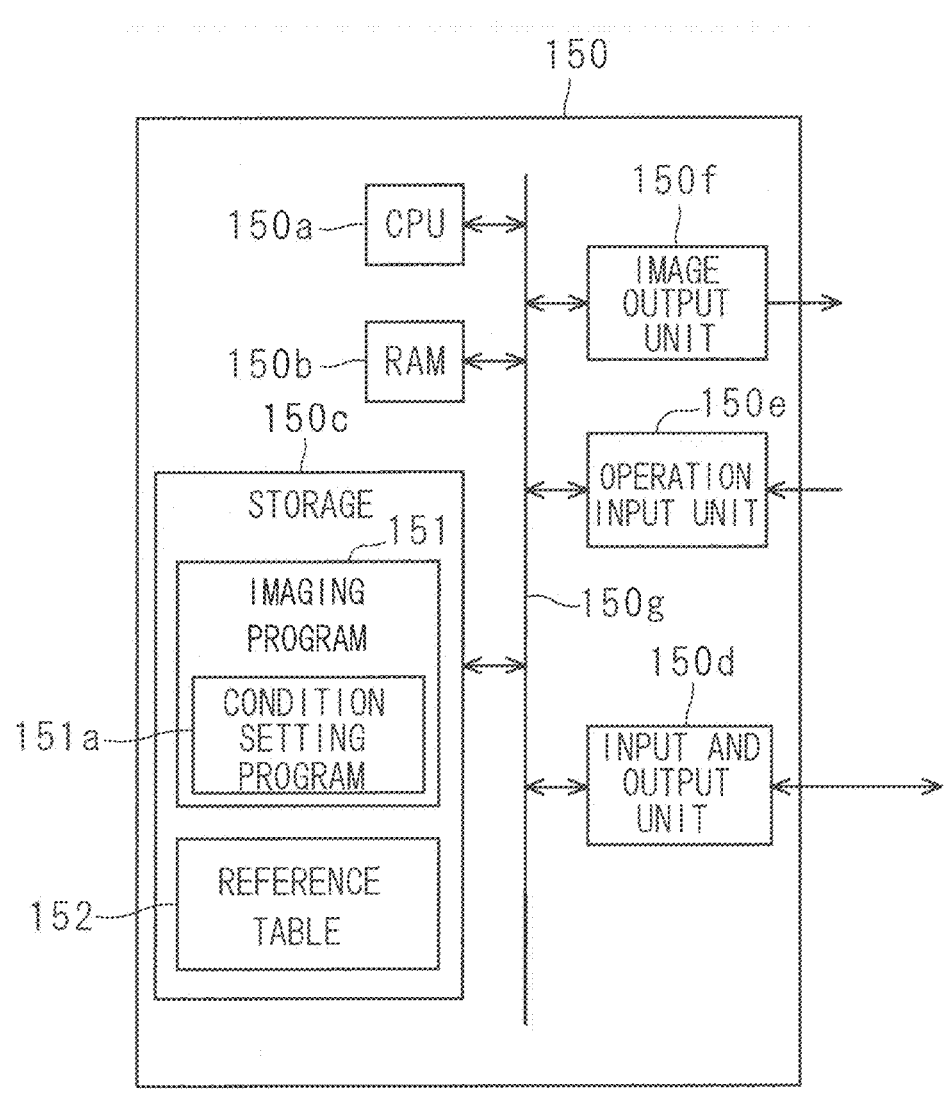

F I G. 1 4

| | | SIZE OF IMAGING AREA | TUBE VOLTAGE | TUBE CURRENT | VOXEL SIZE |
|---|---|---|---|---|---|
| LOW DOSE MODE | ADULT | φ40 | 100kV | 8mA | 80μm |
| | | φ80, φ100 | 100kV | 7mA | 125μm |
| | | φ150 | 100kV | 6mA | 320μm |
| | CHILD | φ40 | 90kV | 8mA | 80μm |
| | | φ80, φ100 | 90kV | 7mA | 125μm |
| | | φ150 | 90kV | 6mA | 320μm |
| HIGH RESOLUTION MODE | ADULT | φ40 | 100kV | 8mA | 80μm |
| | | φ80, φ100 | 100kV | 8mA | 80μm |
| | | φ150 | 100kV | 8mA | 80μm |
| | CHILD | φ40 | 90kV | 8mA | 80μm |
| | | φ80, φ100 | 90kV | 8mA | 80μm |
| | | φ150 | 90kV | 8mA | 80μm |

| | SIZE OF IMAGING AREA | TUBE VOLTAGE | TUBE CURRENT | RADIATION TIME |
|---|---|---|---|---|
| ADULT | φ40 | 100kV | 8mA | 17.9s |
| | φ80, φ100 | 100kV | 8mA | 9.4s |
| | φ150 | 100kV | 6mA | 9.4s |

FIG. 18

| IMAGING PURPOSE | TUBE VOLTAGE | TUBE CURRENT |
|---|---|---|
| · TOOTH ROOT FRACTURE<br>· ENDODONTIC TREATMENT<br>· PERIAPICAL LESION<br>· BONE REGENERATION PROCESS OF IMPLANT | 100 kV | 8 mA |
| · PERIODONTAL · WISDOM TOOTH<br>· EXCESSIVE TOOTH<br>· BURIED TOOTH<br>· SALIVARY STONE | 100 kV | 6 mA |

FIG. 19

| IMAGING REGION | TUBE VOLTAGE | TUBE CURRENT |
|---|---|---|
| · LOWER ANTERIOR TOOTH<br>· MANDIBULAR MOLAR<br>· UPPER ANTERIOR TOOTH<br>· MAXILLARY MOLAR | 100 kV | 6 mA |
| · TEMPOROMANDIBULAR JOINT | 100 kV | 8 mA |

F I G. 2 0

| SIZE OF IMAGING RANGE | IMAGING PURPOSE | IMAGING REGION | X-RAY OUTPUT SETTING | IMAGE QUALITY SETTING |
|---|---|---|---|---|
| φ40 | TOOTH ROOT FRACTURE, PERIAPICAL LESION, BONE REGENERATION PROCESS of IMPLANT | LOWER ANTERIOR TOOTH | 100kV, 5mA, 17.9s | VOXEL SIZE:80μm |
| | | MANDIBULAR MOLAR, UPPER ANTERIOR TOOTH | 100kV, 6mA, 17.9s | |
| | | MAXILLARY MOLAR | 100kV, 8mA, 17.9s | |
| | PERIODONTAL, WISDOM TOOTH, EXCESSIVE TOOTH, BURIED TOOTH, SALIVARY STONE | LOWER ANTERIOR TOOTH | 100kV, 4mA, 9.4s | VOXEL SIZE:125μm |
| | | MANDIBULAR MOLAR, UPPER ANTERIOR TOOTH | 100kV, 5mA, 9.4s | |
| | | MAXILLARY MOLAR | 100kV, 6mA, 9.4s | |

MEDICAL X-RAY CT IMAGING APPARATUS, MEDICAL X-RAY RAY CT IMAGING CONDITION SETTING METHOD, AND NON-TRANSITORY COMPUTER READABLE MEDIUM

CROSS-REFERENCES TO RELATED APPLICATIONS

This application claims priority to Japanese Patent Application No. 2017-207855, filed Oct. 27, 2017, and Japanese Patent Application No. 2018-198351, file Oct. 22, 2018. The contents of both applications are herein incorporated by reference in their entirety.

BACKGROUND

Technical Field

The present invention relates to a technique of setting an imaging condition in a medical X-ray CT imaging apparatus.

Description of the Background Art

Japanese Patent Application Laid-Open No. 2005-80748 discloses that adult input or child input is performed based on whether a patient is an adult or a child and that age is input. Japanese Patent Application Laid-Open No. 2005-80748 also discloses that the highest priority target such as an exposure dose, image quality, and an imaging speed is input. An X-ray CT imaging apparatus of Japanese Patent Application Laid-Open No. 2005-80748 discloses that an optimum imaging condition is automatically set based on the adult or child input and the highest priority target input.

Published Japanese Translation of PCT Application No. 2014-528284 discloses that a CT scanning parameter is derived according to a physique of the patient.

BRIEF SUMMARY

In performing X-ray CT imaging, radiation exposure is preferably decreased as low as possible.

However, when the imaging condition is set depending on the adult or child, or the physique, sometimes an appropriate CT image can hardly be obtained according to a diagnostic purpose. For example, sometimes the sharp X-ray CT image of a local area needs to be obtained even in the case that the X-ray CT imaging is performed on the child or a person having the small physique. Even in the case that the X-ray CT imaging is performed on the adult or a person having the large physique, sometimes it is sufficient to obtain a wide range of the X-ray CT image, and such sharpness is not required.

An object is to obtain an X-ray CT image with appropriate image quality as much as possible according to an imaging purpose while the radiation exposure is decreased as low as possible.

According to a first aspect, a medical X-ray CT imaging apparatus includes: an X-ray generator that generates a cone beam; an X-ray detector; a support that supports the X-ray generator and the X-ray detector while the X-ray generator and the X-ray detector are opposed to each other; a turning drive unit that turns the X-ray generator and the X-ray detector, which are supported by the support; an imaging information receiving unit that receives a setting of an imaging area relating to at least one of a size of the imaging area, an imaging purpose, and an imaging region; and an X-ray output condition setting unit that automatically sets an output condition of the X-ray generator according to at least one of the size of the imaging area, the imaging purpose, and the imaging region, which are received by the imaging information receiving unit.

Consequently, the radiation exposure can be decreased as low as possible by automatically setting the output condition of the X-ray generator according to at least one of the size of the imaging area, the imaging purpose, and the imaging region, which are received. When the size of the imaging area or the imaging region is typically set according to the imaging purpose, the X-ray CT image having the adequate image quality can be obtained according to the imaging purpose by automatically setting the output condition of the X-ray generator according to at least one of the size of the imaging area, the imaging purpose, and the imaging region.

A second aspect is the medical X-ray CT imaging apparatus according to the first aspect further including an image quality setting unit that automatically sets image quality of an X-ray CT image according to at least one of the setting of the imaging area received by the imaging information receiving unit and the output condition of the X-ray generator set by the X-ray output condition setting unit.

The noise is easily included in the X-ray CT image under the X-ray output condition aimed at the low dose. For this reason, as in the second aspect, the noise can be reduced by automatically setting the image quality of the X-ray CT image according to at least one of the setting of the imaging area and the output condition of the X-ray generator.

A third aspect is the medical X-ray CT imaging apparatus according to the first or second aspect, and the imaging information receiving unit receives the setting of the size of the imaging area on a plane orthogonal to a turning axis of the turning drive unit as the setting relating to the size of the imaging area.

Consequently, the output condition of the X-ray generator can automatically be set according to the size in the plane orthogonal to the turning axis.

A fourth aspect is the medical X-ray CT imaging apparatus according to any one of the first to third aspects, the imaging information receiving unit can receive settings of a first imaging area and a second imaging area wider than the first imaging area as the setting relating to the size of the imaging area, and the X-ray output condition setting unit automatically sets at least one setting value defining a first output condition and a second output condition such that a dose based on the second output condition corresponding to the size of the second imaging area is smaller than a dose based on the first output condition corresponding to the size of the first imaging area.

For the setting of the relatively small first imaging area, the X-ray CT imaging can be performed under the first output condition that the dose becomes relatively large. On the other hand, for the setting of the relatively large second imaging area, the X-ray CT imaging can be performed under the second output condition that the dose becomes relatively small.

A fifth aspect is the medical X-ray CT imaging apparatus according to the fourth aspect, and the imaging information receiving unit can receive a setting of an area, where a maxillofacial area of a subject is set to the imaging area and a tooth of a part of a dental arch is contained, to the first imaging area and a setting of an area, where the maxillofacial area of the subject is set to the imaging area and an entire area of the dental arch or all the teeth of the dental arch are contained, to the second imaging area.

Consequently, in the case that the area in which a part of the teeth of the dental arch is contained is set as the first imaging area, the X-ray CT imaging can be performed under the first output condition that the dose becomes relatively large, and the observation can be performed with the relatively sharp image. On the other hand, in the case that the area in which the entire area of the dental arch or all the teeth of the dental arch is contained is set as the second imaging area, the X-ray CT imaging can be performed under the second output condition that the dose becomes relatively small.

A sixth aspect is the medical X-ray CT imaging apparatus according to the fourth aspect, and the imaging information receiving unit can receive a setting of an imaging area where a boundary circle or a circumscribed circle has a diameter of R1 (mm) as the first imaging area while receiving a setting of an imaging area where a boundary circle or a circumscribed circle has a diameter of R2 (mm) as the second imaging area, where, for a value k1 satisfying 40 (mm)<k1 (mm)<70 (mm), an expression of R1 (mm)<k1 (mm)<R2 (mm) is satisfied.

Consequently, the observation can be performed with the relatively sharp image in the case that the X-ray CT imaging is performed on a part of the dental arch. On the other hand, when R2 is larger than k1, the X-ray CT imaging can be performed under the second output condition that the dose becomes relatively small. For this reason, the X-ray CT imaging can be performed with the relatively low dose in the case that the X-ray CT imaging is performed on the entire dental arch.

A seventh aspect is the medical X-ray CT imaging apparatus according to the fourth aspect, and the imaging information receiving unit can receive a setting of an imaging area where a boundary circle or a circumscribed circle has a diameter of R1 (mm) as the first imaging area while receiving a setting of an imaging area where a boundary circle or a circumscribed circle has a diameter of R2 (mm) as the second imaging area, where, for a value k2 satisfying 80 (mm)<k2 (mm)<120 (mm), an expression of R1 (mm) <k2 (mm)<R2 (mm) is satisfied.

Consequently, the observation can be performed with the relatively sharp image in the case that the X-ray CT imaging is performed on the entire dental arch and so on. On the other hand, when R2 is larger than k1, the X-ray CT imaging can be performed under the second output condition that the dose becomes relatively small. For this reason, the X-ray CT imaging can be performed with the relatively low dose in the case that the X-ray CT imaging is performed on the entire jaw and so on.

An eighth aspect is the medical X-ray CT imaging apparatus according to any one of the first to seventh aspects, the imaging information receiving unit can receive a setting of a physique, and the X-ray output condition setting unit automatically sets the output condition of the X-ray generator according to the setting of the physique in addition to the setting of the imaging area relating to at least one of the size of the imaging area, the imaging purpose, and the imaging region, which are received by the imaging information receiving unit.

Consequently, the radiation exposure can be decreased as low as possible while the physique in addition to at least one of the size of the imaging area, the imaging purpose, and the imaging region is taken into consideration. The X-ray CT image having appropriate image quality can be obtained by taking the physique.

A ninth aspect is the medical X-ray CT imaging apparatus according to the eighth aspect, the imaging information receiving unit receives a setting whether a subject is a physique of a child or a physique exceeding the physique of the child as the setting of the physique, and the X-ray output condition setting unit automatically sets at least one setting value defining an output condition corresponding to the physique exceeding the physique of the child and an output condition corresponding to the physique of the child such that a dose based on the output condition corresponding to the physique exceeding the physique of the child is larger than a dose based on the output condition corresponding to the physique of the child.

Consequently, when the subject is set to the child as the setting of the physique, the dose can be decreased and the exposure dose can be decreased. On the other hand, when the subject is set to the physique exceeding the child, the sharp image can be obtained by increasing the dose.

A tenth aspect is the medical X-ray CT imaging apparatus according to any one of the first to ninth aspects, the imaging information receiving unit receives the setting of the imaging purpose, and the X-ray output condition setting unit automatically sets the output condition of the X-ray generator according to the imaging purpose received by the imaging information receiving unit.

Consequently, the output condition of the X-ray generator can be automatically set according to the set imaging purpose.

An eleventh aspect is the medical X-ray CT imaging apparatus according to any one of the first to tenth aspects, the imaging information receiving unit receives the setting of the imaging region, and the X-ray output condition setting unit automatically sets the output condition of the X-ray generator according to the imaging region received by the imaging information receiving unit.

Consequently, the output condition of the X-ray generator can automatically be set according to the set imaging region.

A twelfth aspect is the medical X-ray CT imaging apparatus according to any one of the first to eleventh aspects, and the X-ray output condition setting unit automatically sets at least one of a tube voltage of the X-ray generator, a tube current of the X-ray generator, and time during which the X-ray generator emits an X-ray as the output condition of the X-ray generator.

Consequently, the dose can be adjusted by setting at least one of the tube voltage and the tube current of the X-ray generator and the time during which the X-ray generator emits the X-ray.

A thirteenth aspect is the medical X-ray CT imaging apparatus according to any one of first to twelfth aspects further including a mode setting receiving unit that receives settings of a low dose mode and a high resolution mode, and the X-ray output condition setting unit automatically sets the output condition of the X-ray generator according to the imaging area received by the imaging information receiving unit when the low dose mode is received by the mode setting receiving unit.

Consequently, the output condition of the X-ray generator is automatically set according to the received imaging area when the low dose mode is received, which allows the X-ray CT image having the appropriate image quality to be obtained according to the purpose of imaging while the exposure dose is decreased as low as possible.

A fourteenth aspect is the medical X-ray CT imaging apparatus according to any one of the first to thirteenth aspects further including an output condition setting receiving unit that receives a manual setting of the output condition of the X-ray generator, and the X-ray output condition setting unit changes the output condition of the X-ray generator according to the manual setting received by the output condition setting receiving unit after automatically setting the output condition of the X-ray generator according to the imaging area received by the imaging information receiving unit.

Consequently, the output condition of the X-ray generator, which is set according to the imaging area, can be changed by the manual setting according to operator's preference.

To solve the above problem, according to a fifteenth aspect, a medical X-ray CT imaging condition setting method for setting a condition in performing X-ray CT imaging in a medical X-ray CT imaging apparatus including: an X-ray generator that generates a cone beam; an X-ray detector; a support that supports the X-ray generator and the X-ray detector while the X-ray generator and the X-ray detector are opposed to each other; and a turning drive unit that turns the X-ray generator and the X-ray detector, which are supported by the support, the medical X-ray CT imaging condition setting method includes the steps of a processor for: receiving a setting of an imaging area relating to at least one of a size of the imaging area, an imaging purpose, and an imaging region; and setting automatically an output condition of the X-ray generator according to at least one of the size of the imaging area, the imaging purpose, and the imaging region, which are received.

Consequently, the radiation exposure can be decreased as low as possible by automatically setting the output condition of the X-ray generator according to at least one of the size of the imaging area, the imaging purpose, and the imaging region, which are received. When the size of the imaging area or the imaging region is typically set according to the imaging purpose, the X-ray CT image having the adequate image quality can be obtained according to the imaging purpose by automatically setting the output condition of the X-ray generator according to at least one of the size of the imaging area, the imaging purpose, and the imaging region.

To solve the above problem, according to a sixteenth aspect, a non-transitory computer readable medium for a medical X-ray CT imaging apparatus including: an X-ray generator that generates a cone beam; an X-ray detector; a support that supports the X-ray generator and the X-ray detector while the X-ray generator and the X-ray detector are opposed to each other; and a turning drive unit that turns the X-ray generator and the X-ray detector, which are supported by the support, the non-transitory computer readable medium in which an X-ray CT imaging condition setting program is recorded, the X-ray CT imaging condition setting program causes a computer that sets an X-ray CT imaging condition of the medical X-ray CT imaging apparatus to perform the steps of: (a) receiving a setting of an imaging area relating to at least one of a size of the imaging area, an imaging purpose, and an imaging region; and (b) setting automatically an output condition of the X-ray generator according to at least one of the size of the imaging area, the imaging purpose, and the imaging region, which are received.

Consequently, the radiation exposure can be decreased as low as possible by automatically setting the output condition of the X-ray generator according to at least one of the size of the imaging area, the imaging purpose, and the imaging region, which are received. When the size of the imaging area or the imaging region is typically set according to the imaging purpose, the X-ray CT image having the adequate image quality can be obtained according to the imaging purpose by automatically setting the output condition of the X-ray generator according to at least one of the size of the imaging area, the imaging purpose, and the imaging region.

To solve the above problem, according to a seventeenth aspect, a medical X-ray CT imaging apparatus comprising: an X-ray generator that generates a cone beam; an X-ray detector; a support that supports the X-ray generator and the X-ray detector while the X-ray generator and the X-ray detector are opposed to each other; an actuator that turns the X-ray generator and the X-ray detector, which are supported by the support; and a processor, wherein, when a setting of an imaging area relating to at least one of a size of the imaging area, an imaging purpose, and an imaging region is input as imaging information, the processor sets automatically an output condition of the X-ray generator according to at least one of the size of the imaging area, the imaging purpose, and the imaging region, which are input.

Consequently, the radiation exposure can be decreased as low as possible by automatically setting the output condition of the X-ray generator according to at least one of the size of the imaging area, the imaging purpose, and the imaging region, which are received. When the size of the imaging area or the imaging region is typically set according to the imaging purpose, the X-ray CT image having the adequate image quality can be obtained according to the imaging purpose by automatically setting the output condition of the X-ray generator according to at least one of the size of the imaging area, the imaging purpose, and the imaging region.

An eighteenth aspect is the medical X-ray CT imaging apparatus according to seventeenth aspect, the processor can receive settings of a first imaging area and a second imaging area wider than the first imaging area as the setting relating to the size of the imaging area, and automatically sets at least one setting value defining a first output condition and a second output condition such that a dose based on the second output condition corresponding to the size of the second imaging area is smaller than a dose based on the first output condition corresponding to the size of the first imaging area.

Consequently, the X-ray CT imaging can be performed under the first output condition that the dose becomes relatively large. On the other hand, for the setting of the relatively large second imaging area, the X-ray CT imaging can be performed under the second output condition that the dose becomes relatively small.

A nineteenth aspect is the medical X-ray CT imaging apparatus according to seventeenth or eighteenth aspect, the processor can receive settings of a first imaging purpose and a second imaging purpose where the first imaging purpose is an imaging purpose intending a more detailed observation than the second imaging purpose as the setting relating to the imaging purpose, and automatically sets at least one setting value defining a first output condition and a second output condition such that a dose based on the second output condition corresponding to the second imaging purpose is smaller than a dose based on the first output condition corresponding to the first imaging purpose. Consequently, the output condition of the X-ray generator can be automatically set according to the set imaging purpose.

A twentieth aspect is the medical X-ray CT imaging apparatus according to any one of seventeenth to nineteenth aspect, the processor can receive settings of a first imaging region and a second imaging region where the first imaging region includes a greater amount of hard tissues than that of the second imaging region or hard tissue density of the first imaging region is higher than that of the second imaging region as the setting relating to the imaging region, and automatically sets at least one setting value defining a first output condition and a second output condition such that a dose based on the second output condition corresponding to the second imaging region is smaller than a dose based on the first output condition corresponding to the first imaging region.

Consequently, the output condition of the X-ray generator can be automatically set according to the amount of hard tissues or hard tissue density.

A twenty-first aspect is the medical X-ray CT imaging apparatus according to any one of seventeenth to twentieth aspect, the processor automatically sets image quality of an X-ray CT image according to at least one of the setting of the imaging area input thereby and the set output condition of the X-ray generator.

Consequently, the noise can be reduced by automatically setting the image quality of the X-ray CT image according to at least one of the setting of the imaging area and the output condition of the X-ray generator.

These and other objects, features, aspects and advantages of the present invention will become more apparent from the following detailed description of the present invention when taken in conjunction with the accompanying drawings.

BRIEF DESCRIPTION OF THE DRAWINGS

FIG. 6 is a block diagram illustrating an electrical configuration of a main body controller;

FIG. 14 is a view illustrating an example of a reference table;

FIG. 18 is a view illustrating another example of the reference table;

FIG. 19 is a view illustrating another example of the reference table; and

FIG. 20 is a view illustrating another example of the reference table.

DETAILED DESCRIPTION OF THE PREFERRED EMBODIMENTS

First Preferred Embodiment

Figure 1:
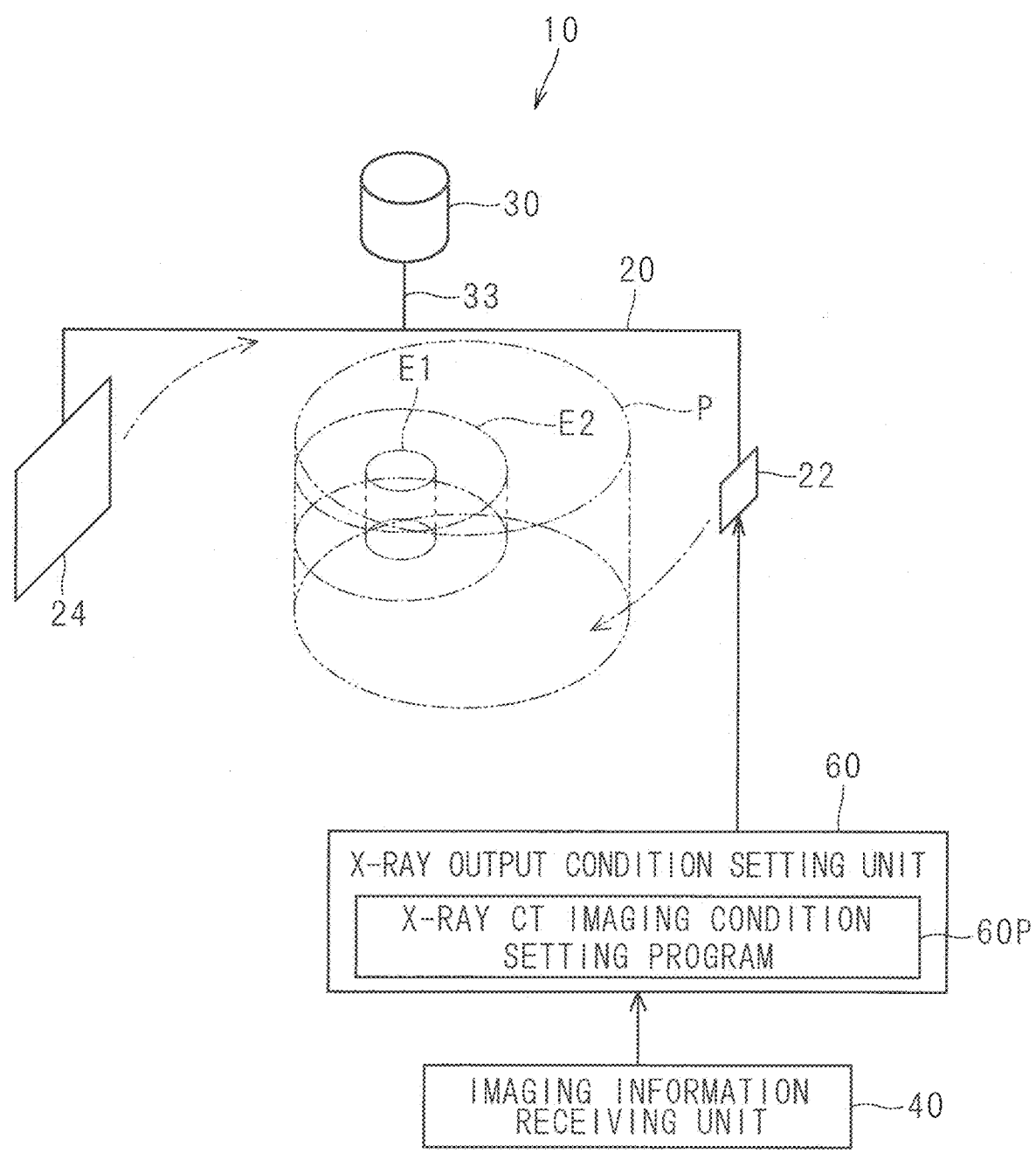
FIG. 1 is a schematic diagram illustrating an X-ray CT imaging apparatus according to a first preferred embodiment.

Hereinafter, a medical X-ray CT imaging apparatus, a medical X-ray CT imaging condition setting method, and an X-ray CT imaging condition setting program according to a first preferred embodiment will be described. FIG. 1 is a schematic diagram illustrating an X-ray CT imaging apparatus 10.

The X-ray CT imaging apparatus 10 is an apparatus that performs X-ray CT (Computed Tomography) imaging of a subject P, and includes an X-ray generator 22, an X-ray detector 24, a support 20, a turning drive unit 30, an imaging information receiving unit 40, and an X-ray output condition setting unit 60.

The X-ray generator 22 emits an X-ray cone beam. The X-ray detector 24 detects the X-ray cone beam emitted from the X-ray generator 22.

The support 20 supports the X-ray generator 22 and the X-ray detector 24 while the X-ray generator 22 and the X-ray detector 24 are opposed to each other. A space where the subject P is disposed between the X-ray generator 22 and the X-ray detector 24 is provided while the X-ray generator 22 and the X-ray detector 24 are supported by the support 20. For example, the subject P is a human head. The X-ray cone beam emitted from the X-ray generator 22 passes through the subject P, and is incident on the X-ray detector 24. The X-ray incident on the X-ray detector 24 is converted into an electric signal corresponding to intensity of the X-ray in each unit pixel. An X-ray CT image is generated based on each electric signal.

The turning drive unit 30 turns the X-ray generator 22 and the X-ray detector 24, which are supported by the support 20. For example, the turning drive unit 30 includes an electric motor, and includes an acceleration and deceleration mechanism such as a gear as necessary. The turning drive unit 30 rotatably supports a shaft 33 protruding from the support 20 at a position between the X-ray generator 22 and the X-ray detector 24. With a central axis of the shaft 33 as a turning center, the support 20 turns by driving the turning drive unit 30. As a result, the X-ray generator 22 and the X-ray detector 24 turn around the subject P.

The imaging information receiving unit 40 is configured to be able to receive a setting of the imaging area. The imaging information receiving unit 40 can receive the setting of the imaging area by receiving an input operation of an operator through, for example, a touch panel or an operation switch.

The setting of the imaging area includes information about at least one of the size of the imaging area where the X-ray CT imaging needs to be performed with respect to the subject P, the imaging purpose, and the imaging region.

For example, assuming that the medical X-ray CT imaging apparatus is a dental X-ray CT imaging apparatus, the size of the imaging area may include a setting including the size of the imaging area specifying a part of a row of teeth (for example, an area including one to three teeth), a setting including the size of the imaging area specifying the entire row of teeth, and a setting including the size of the imaging area specifying an entire jaw. For example, the size of the imaging area can be set by the size of a radius indicating the size of the imaging area and by the imaging area for the row of teeth or a jaw area illustrated by the drawing.

Here, the imaging area will be described. The configuration of the present application can be suitably applied to the partial area with respect to the whole subject as the living thing of the individual. Partial areas such as the head, chest, abdomen, etc. exist in the entire subject. In the head, there are more subdivided areas such as a maxillofacial area which is a clinical specialty for dentistry and an ear-and-nose area which is a clinical specialty for otorhinology. As described above, there are partial areas in the whole subject individual, and there may be a magnitude relation also among the partial areas.

Of the whole individual, the head, as a target, is considered that the head portion as a first layer partial area, the jaw area therein as a second layer partial area, the dental arch area therein as a third layer partial area, the anterior tooth area in the third area as a fourth layer partial region, and so forth, and the size of the region may be considered by the depth of the layer concerning the size of the region. In this case, the layer having a wide area may be regarded as a shallow layer, and the layer having a narrow area may be considered as a deep layer. The stratum may be appropriately provided according to occasion, and it may be allowed to consider that the dental arch region as a first layer partial region and the partial areas in the middle dental arch, such as an anterior tooth area and a molar area, as a second layer partial region.

In the case of the otorhinology area, an example can be considered that the ear-and-nose area to be considered as a first layer partial region and the ossicular region is considered as the second layer partial region.

In this manner, partial areas may be set for each category of medical care subjects.

The partial region of the shallow layer does not necessarily completely include the partial region of the deep layer and the partial region of the deep layer may have a portion protruding from the partial region of the shallow layer.

Example of the imaging purpose may include any one of observation purposes of a tooth root fracture, an endodontic treatment, a periapical lesion, a bone regeneration process of implant, a periodontal, a wisdom tooth, an excessive tooth, a buried tooth, and a salivary stone.

Example of the imaging region may include any one of a lower anterior tooth, a mandibular molar, an upper anterior tooth, a maxillary molar, all teeth, a temporomandibular joint, and a face.

The X-ray output condition setting unit 60 automatically sets the output condition of the X-ray generator 22 according to the size of the imaging area received by the imaging information receiving unit 40.

The X-ray output condition setting unit 60 includes at least one processor. For example, the X-ray output condition setting unit 60 is constructed with a computer including at least one processor, a random access memory (RAM), a storage, and an input and output unit. The storage is constructed with a non transitory computer readable medium such as a flash memory or a hard disk device, and stores an X-ray CT imaging condition setting program 60P for setting an X-ray output condition and the like. The RAM serves as a work area when at least one processor performs predetermined processing. At least one processor performs predetermined processing according to the X-ray CT imaging condition setting program 60P stored in the storage, and sets the X-ray CT imaging condition. In terms of setting the X-ray CT imaging condition, the output condition of the X-ray generator 22 according to the size of the imaging area accepted by the imaging information receiving unit 40 is automatically set.

At this point, the output condition of the X-ray generator 22 is automatically set according to the size of the imaging area in order to adjust the dose to the subject P according to the size of the imaging area. That is, for example, the output condition of the X-ray generator 22 is a condition that influences the dose to the subject P in performing the X-ray CT imaging. Here, the dose may be defined from the amount of X-ray emitted from the X-ray tube which is the X-ray source of the X-ray generator 22. This output amount can be adjusted by the amount of energy applied to the X-ray tube. For example, when X-ray irradiation with a tube current of 40 mA and X-ray irradiation with 50 mA are performed at the same tube voltage and the same irradiation time, the output amount is larger for 50 mA than for 40 mA, and when X-ray irradiation with the tube voltage of 40 kV and X-ray irradiation with 50 kV are performed at the same tube current and the same irradiation time, the output amount is larger for 50 kV than for 40 kV. The output amount can also be adjusted from the irradiation time. For example, suppose an X-ray irradiation for a short time with the same tube current and tube voltage and an X-ray irradiation for a long time, the longer the irradiation time is, the larger the output amount is for the longer irradiation time. Supposing that an X-ray cone beam shape adjuster 127 regulates the irradiating X-ray to be in the cone beam shape, it is assumed that in an X-ray cone beam path to be irradiated, if there is nothing to block between the X-ray generator 22 and the X-ray detector 24, the amount of light received by the detection surface of the X-ray detector 24 becomes larger when the output amount is larger.

The dose may be the amount of X-ray irradiated to a unit three-dimensional region per unit of the three-dimensional region geometrically formed between a focus of the X-ray tube and an X-ray receiving surface. In the case where a cylindrical region having a diameter of 40 mm and a height of 40 mm is to be irradiated with X ray, it is assumed that the X-ray cone beam shape adjuster 127 regulates the irradiation X-ray so that only the region is irradiated with X-ray, when it is received by the detection surface of the X-ray detector 24, and then it is assumed that the light receiving surface has a width of 60 mm and a height of 60 mm. A quadrangular pyramidal three-dimensional region is geometrically formed between the focus of the X-ray tube of the X-ray generator 22 and the light receiving surface having the width of 60 mm and the height of 60 mm When this light receiving surface is further subdivided into, for example, a unit area region with a width of 1 mm and a height of 1 mm, a superfine quadrangular pyramidal three-dimensional region is formed between the focus of the X-ray tube and the unit area of 1 mm in width and 1 mm in height. The superfine three-dimensional region obtained by subdividing the quadrangular pyramidal three-dimensional region may be regarded as a unit three-dimensional region, and the amount of X-ray irradiated to the unit three-dimensional region may be used as the dose. As will be described later, the unit area region may be a pixel unit constituting the detection surface of the X-ray detector 24 (128).

The dose is unchanged even if the subject is not present in the unit three-dimensional region. When a subject is present, the X-ray irradiated in the unit three-dimensional region is absorbed by the subject and does not reach the detection surface of the X-ray detector 24 or reaches but attenuated. Meanwhile, when the subject is not present, all the X-rays irradiated into the unit three-dimensional region are received by the detection surface of the X-ray detector 24 (The amount absorbed by air is negligible because it is a trace amount.). In any case, as long as X-ray irradiation is performed under the same conditions, the amounts of X-ray irradiated into the unit three-dimensional region are the same as the amount. For example, assuming that X-ray irradiation is performed with each output amount of large and small, and measuring the dose in the unit three-dimensional region, the measured dose is higher in the X-ray irradiation with a larger output amount than in the X-ray irradiation with a smaller output amount.

In this example, if it is assumed that X-ray irradiations is performed with respect to the same part range of the same subject positioned in the same posture with large and small output amounts, consequently, if the X-ray output amount is large, the energy due to the X-ray absorbed in the unit mass portion of the subject P also becomes large, and if the output amount of the X-ray is small, the energy due to the X-ray absorbed in the unit mass portion of the subject P also becomes small.

In setting the X-ray output condition, the measured value of the specific dose may not necessarily be obtained. This is because, for example, setting an appropriate output amount is ensured if the knowledge that the output amount from which an excellent X-ray image can be obtained is theoretically, experimentally, and empirically possessed. It is sufficient that one can estimate the prospect that the expected result can be obtained if the dose is measured.

Also, the dose is represented by energy of X-ray absorbed by a unit mass portion of the subject P in the case that the subject P is present in the irradiation range of X-ray, and may be represented by, for example, an absorbed dose. In performing the X-ray CT imaging, for example, the absorbed dose is increased when the tube voltage of the X-ray tube constituting the X-ray generator 22 is increased, and the absorbed dose is increased when the tube current is increased. The absorbed dose is increased when an X-ray irradiation time is lengthened in performing the X-ray CT imaging. Thus, example of the output condition of the X-ray generator 22 includes at least one of the tube voltage, the tube current, the X-ray irradiation time in performing the X-ray CT imaging. For example, the X-ray irradiation time may be set by a speed (rotation speed) at which the X-ray generator 22 and the X-ray detector 24 are turned by the turning drive unit 30 and a range (for example, 360° turning or 180° turning) where the X-ray generator 22 and the X-ray detector 24 are turned by the turning drive unit 30. The dose is appropriately adjusted by appropriately setting these output conditions. In this manner, as the amount of X-ray increases in the case that the subject P is present in the irradiation range of the X-ray, the amount of X-ray absorbed in the unit mass portion of the subject P also increases as the result. Therefore, both one definition and the other definition can be applied to a common X-ray radiation to define the dose according to the situation.

Figure 2:
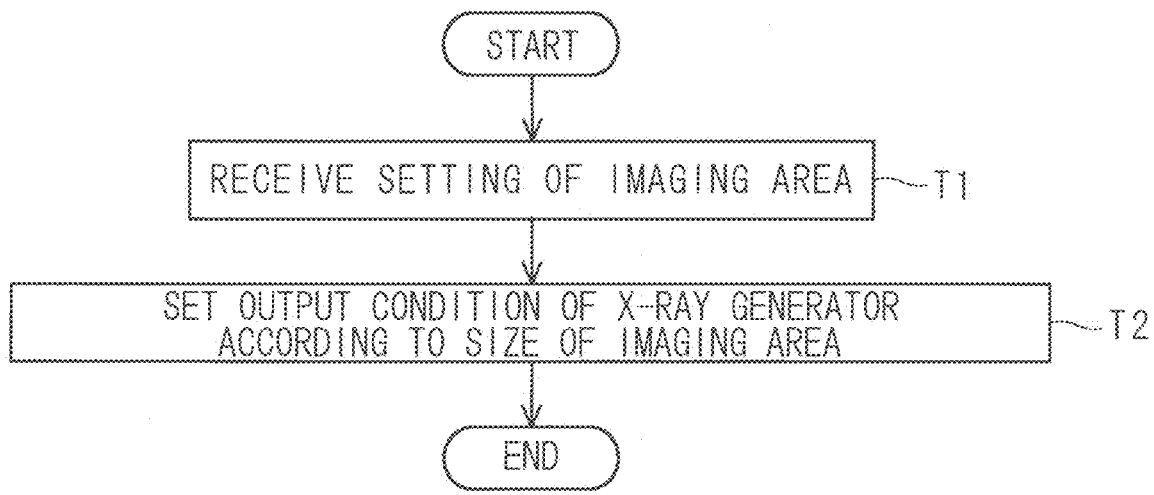
FIG. 2 is a flowchart illustrating processing performed by an X-ray output condition setting unit.

FIG. 2 is a flowchart illustrating processing performed by the X-ray output condition setting unit 60.

That is, in performing the X-ray CT imaging, the imaging area set by an operator is received through the imaging information receiving unit 40 in step T1. Reception is made by input, for example. The setting relating to the imaging area includes the setting relating to at least one of the size of the imaging area, the imaging purpose, and the imaging region.

In step T2, the output condition of the X-ray generator is automatically set according to at least one of the size of the imaging area, the imaging purpose, and the imaging region.

For example, as illustrated in FIG. 1, it is conceivable that the size of the imaging area is an imaging area E1 or an imaging area E2 wider than the imaging area E1.

In this case, for example, a first output condition is set for the relatively narrow (a first spread) imaging area E1, and a second output condition is set for the relatively wide (a second spread) imaging area E2. For example, the dose in the first output condition is defined as a first dose while the dose in the second output condition is defined as a second dose, and the first output condition and the second output condition are set such that the first dose is larger than the second dose. For the relatively narrow imaging area E1, the X-ray CT imaging is usually performed for the purpose of observing a local area in detail, so that the relatively sharp image can be obtained by performing the X-ray CT imaging under the first output condition that the dose becomes relatively large. For the relatively wide imaging area E2, the X-ray CT imaging is usually performed for the purpose of the overall observation, so that low radiation exposure can be achieved by performing the X-ray CT imaging under the second output condition that the dose becomes relatively small.

For example, the first output condition is set in the case that an observation for any one of the tooth root fracture, the endodontic treatment, the periapical lesion, and the bone regeneration process of the implant is set as a first imaging purpose for the imaging purpose, and the second output condition is set in the case that an observation for any one of the periodontal, the wisdom tooth, the excessive tooth, the buried tooth, and the salivary stone is set as a second imaging purpose for the imaging purpose. For example, the first output condition and the second output condition are set such that the dose in the first output condition is larger than the dose in the second output condition. In the case that the observation of any one of the tooth root fracture, the endodontic treatment, the periapical lesion, and the bone regeneration process of the implant is set as the imaging purpose, the X-ray CT imaging is usually performed in order to observe the target region in detail, so that the relatively sharp image can be obtained by performing the X-ray CT imaging under the first output condition that the dose becomes relatively large. In the case that the observation of any one of the periodontal, the wisdom tooth, the excessive tooth, the buried tooth, and the salivary stone is set as the imaging purpose, the X-ray CT imaging is usually performed for the purpose of overall observation, so that the low radiation exposure can be achieved by performing the X-ray CT imaging under the second output condition that the dose becomes relatively small.

When a detailed observation such as an observation of any one of the tooth root fracture, the endodontic treatment, the periapical lesion, and the bone regeneration process of implant, is intended, such a purpose is called the detailed observation purpose, and when a conditional observation where an overall conditional observation or a general conditional observation is intended such as an observation of any one of the periodontal, the wisdom tooth, the excessive tooth, the buried tooth, and the salivary stone, such a purpose is called the regular observation purpose.

X-ray CT imaging for achieving the detailed observation purpose is called the detailed observation CT imaging and X-ray CT imaging for achieving the regular observation purpose is called the regular observation CT imaging. An operational condition that enables the detailed observation purpose CT imaging is referred to as the detailed observation CT imaging mode, and an operational condition that enables the regular observation CT imaging is referred to as the regular observation CT imaging mode.

In the case that the same region is imaged with the same size of the X-ray CT imaging area, it is conceivable to change the output condition according to the imaging purpose. For example, the first output condition is set when the X-ray CT imaging is performed on the same area (the size is also the same) including the lower anterior tooth for the purpose of diagnosing the tooth root fracture as the first imaging purpose, and the second output condition is set when the X-ray CT imaging is performed on the same area including the lower anterior tooth for the purpose of observing the salivary stone as the second imaging purpose. In this way, the exposure dose of the area of the lower anterior teeth can be decreased during salivary stone observation. The image that is relatively sharp and suitable for detailed observation can be obtained when the tooth root fracture is diagnosed.

For example, the first output condition is set in the case that any one of the lower anterior tooth, the mandibular molar, the upper anterior tooth, and the maxillary molar is set as a first imaging region for the imaging region, and the second output condition is set in the case that any one of the all teeth, a wide area from the all teeth to the temporomandibular joint, and a facial area is set as a second imaging region for the imaging region. In the case of this example, the first imaging region and the second imaging region have the relationship between the imaging area of the first spread and the imaging area of the second spread since the region has wide and narrow regions. And, for example, the first output condition and the second output condition are set such that the dose in the first output condition is larger than the dose in the second output condition. The X-ray CT imaging is usually performed for the purpose of observing the relatively narrow imaging region in detail in the case that any one of the lower anterior tooth, the mandibular molar, the upper anterior tooth, and the maxillary molar is set as the imaging purpose, so that the relatively sharp image can be obtained by performing the X-ray CT imaging under the first output condition that the dose becomes relatively large. In the case that any one of the all teeth, a wide area extending from the all teeth to the temporomandibular joint, and the facial area is set as the imaging purpose, X-ray CT imaging is performed for overall observation purpose. Accordingly, by performing X-ray CT imaging under the second output condition that the dose becomes relatively small, the low radiation exposure can be achieved.

It is also conceivable to change the output condition in the case that a different region is imaged in the CT imaging area having the same size. For example, it is assumed that the CT imaging area having the same size, as an area including the temporomandibular joint where a skull base exists in the path of the X-ray cone beam (first imaging region) and as an area including the lower anterior tooth where the skull base deviates from the path of the X-ray cone beam (second imaging region), is set. In this case, the imaging purpose may be set or may not be set. In the case that the imaging purpose is set, the same purpose may be used. An irradiation condition for the former, namely, the temporomandibular joint area and an irradiation condition for the latter, namely, the lower anterior tooth area are respectively set, and the exposure dose to the lower anterior tooth area can be reduced such that the first output condition is set to the temporomandibular joint area and such that the second output condition is set to the lower anterior tooth area. For the temporomandibular joint where the skull base exists in the path of the X-ray cone beam, the sharp image can be obtained regardless of the existence of the skull base.

In the case of imaging different parts in the CT imaging area of the same size, another classification may be provided. In the case where a cylindrical region having a diameter of 40 mm and a height of 40 mm is assumed to be an X-ray CT imaging target, based on the amount of hard tissue, it is classified into a molar area and an anterior tooth area, applying the first output condition with the molar area as a region with many hard tissues and applying the second output condition with the front teeth area as a region with a few hard tissues, and the first output condition and the second output condition may be set such that the dose at the first output condition is larger than the dose at the second output condition.

Even in the same anterior teeth area, in the anterior teeth area of the maxilla and the anterior teeth area of the mandible, there are differences that there are many surrounding hard tissues in the anterior teeth area of the maxilla and there are a few surrounding hard tissues in the anterior teeth area of the mandible. Even in the same molar area, in the molar area of the maxilla and the molar area of the mandible, there are differences that there are many surrounding hard tissues in the molar area of the maxilla and there are a few surrounding hard tissues in the molar area of the mandible.

Paying attention to this, for example, the molar area of the maxilla is classified as a first group, the molar area of the mandible and the anterior tooth area of the maxilla are classified as a second group, and the anterior teeth area of the mandible is classified as a third group.

In the relations between the first group and the second group, assuming the first group as the first imaging region, the second group as the second imaging region, the first output condition and the second output condition are regulated so that the dose based on the first output condition corresponding to the first imaging region is larger than the dose based on the second output condition corresponding to the second imaging region.

In the relations between the second group and the third group, assuming the second group as the first imaging region, the third group as the second imaging region, the first output condition and the second output condition are regulated so that the dose based on the first output condition corresponding to the first imaging region is larger than the dose based on the second output condition corresponding to the second imaging region.

The setting example of FIG. 20 described later is such a setting example.

In addition to the setting based on the amount of the hard tissue, setting may be made depending on the density of the hard tissue.

In the above example, the output condition is set based on one of the size of the imaging area, the imaging purpose, and the imaging region. However, the output condition may be set based on a combination of two or all of the size of the imaging area, the imaging purpose, and the imaging region.

The setting processing relating to the X-ray output condition is ended when the output condition of the X-ray generator is automatically set according to at least one of the size of the imaging area, the imaging purpose, and the imaging region.

According to the set output condition of the X-ray generator, the X-ray CT imaging apparatus 10 irradiates the X-ray cone beam from the X-ray generator 22, and detects the X-ray cone beam transmitted through the subject P with the X-ray detector 24 while turning the X-ray generator 22 and the X-ray detector 24 around the subject P with the turning drive unit 30, thereby performing the X-ray CT imaging.

The X-ray CT image is generated based on the data detected by the X-ray detector 24.

In the X-ray CT imaging apparatus 10, the medical X-ray CT imaging condition setting method, and the X-ray CT imaging condition setting program 60P having the above configurations, the low radiation exposure can be achieved as much as possible by automatically setting the output condition of the X-ray generator 22 according to at least one of the received size of said imaging area, imaging purpose and imaging region. When the sizes of the imaging areas E1 and E2 and the imaging region are set according to the imaging purpose, the X-ray CT image having the adequate image quality can be obtained according to the imaging purpose by automatically setting the output condition of the X-ray generator 22 according to at least one of the size of the imaging area, the imaging purpose, and the imaging region.

For example, for the relatively small imaging area E1, the relatively sharp X-ray CT image can be obtained by performing the X-ray CT imaging under the first output condition that the dose becomes relatively large. In the case that the X-ray CT imaging for the relatively narrow imaging area E1 is performed on a part of the teeth of the dental arch, the X-ray CT imaging is usually performed for the purpose of treatment of some teeth of the dental arch. Consequently, the sharp image suitable for treatment can be obtained by obtaining the relatively sharp X-ray CT image. For example, for the relatively large imaging area E2, the X-ray CT imaging can be performed under the low radiation exposure condition by performing the X-ray CT imaging under the second output condition that the dose is relatively small. In the case that the X-ray CT imaging for the relatively wide imaging area E2 is performed on the whole dental arch or the whole jaw area, the X-ray CT imaging is usually performed for the purpose of observing the overall shape of teeth and a skeleton. Consequently, the X-ray CT image suitable for the whole observation can be obtained under the low radiation exposure X-ray CT imaging condition.

For example, in the case that the tooth root fracture, the endodontic treatment, the periapical lesion, or the bone regeneration process of the implant is set as the imaging purpose, the relatively sharp image can be obtained by performing the X-ray CT imaging under the first output condition that the dose becomes relatively large. In the case that any one of the periodontal, the wisdom tooth, the excessive tooth, the buried tooth, and the salivary stone is set, the low radiation exposure can be achieved by performing the X-ray CT imaging under the second output condition that the dose becomes relatively small.

For example, in the case that any one of the lower anterior tooth, the mandibular molar, the upper anterior tooth, and the maxillary molar, which are a part of the dental arch, is set as the imaging region, the relatively sharp image can be obtained by performing the X-ray CT imaging under the first output condition that the dose becomes relatively large. Further, when any one of the all teeth, the temporomandibular joint, and the face, which are wider than the size including the entire dental arch, is set as the imaging region, the low radiation exposure can be achieved by performing the X-ray CT imaging under the second output condition that the dose becomes relatively small.

Second Preferred Embodiment

An X-ray CT imaging apparatus according to a second preferred embodiment will be described.

<Overall Configuration>

Figure 3:
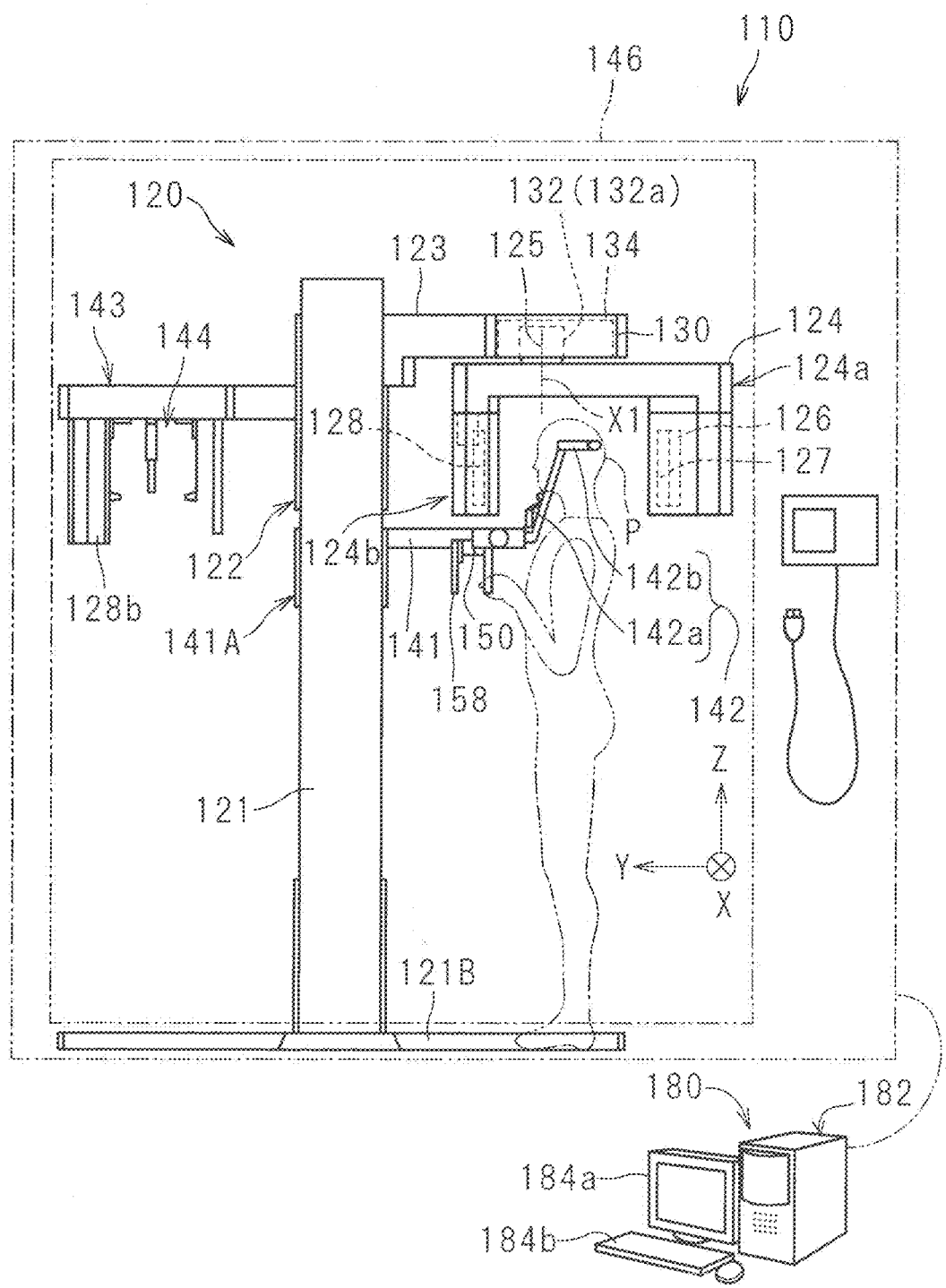
FIG. 3 is a general view illustrating a configuration of an X-ray CT imaging apparatus according to a second preferred embodiment.
Figure 4:
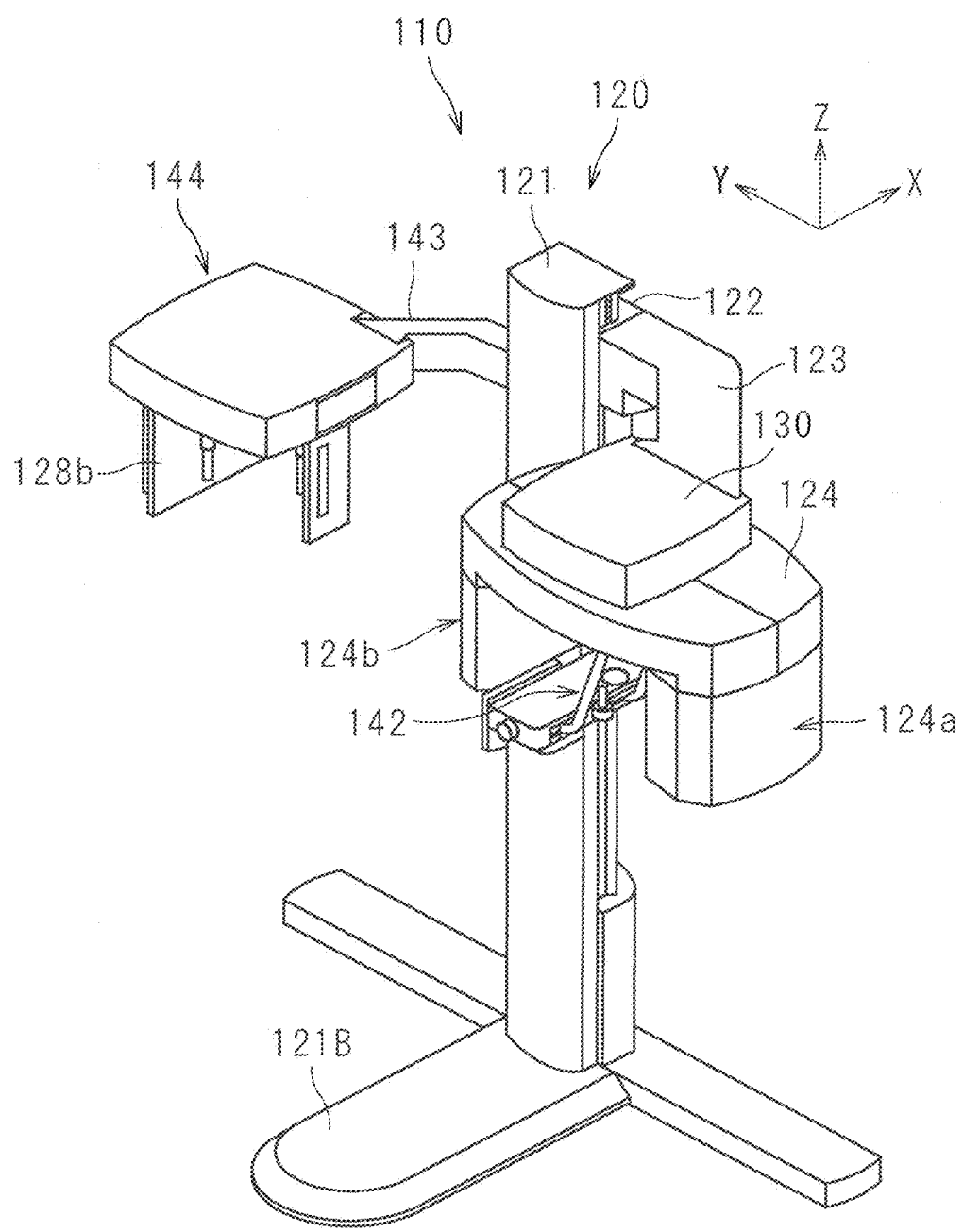
FIG. 4 is a perspective view illustrating the X-ray CT imaging apparatus of the second preferred embodiment when the X-ray CT imaging apparatus is viewed from obliquely above.

FIG. 3 is a general view illustrating a configuration of an X-ray CT imaging apparatus 110 of the second preferred embodiment, and FIG. 4 is a perspective view illustrating the X-ray CT imaging apparatus 110 of the second preferred embodiment when the X-ray CT imaging apparatus 110 is viewed from obliquely above. In FIGS. 3 and 4, for convenience, an XYZ coordinate system may be set in an entire space where the X-ray CT imaging apparatus 110 exists. In the XYZ coordinate system, based on the head P supported in the X-ray CT imaging apparatus 110, a right direction is an X (+) direction, a left direction is an X (−) direction, a forward direction is a Y (+) direction, a backward direction is a Y (−) direction, an upward direction is a Z (+) direction, and a downward direction is a Z (−) direction.

The X-ray CT imaging apparatus 110 includes an imager 120 and an image processing apparatus 180. The imager 120 is an apparatus that collects X-ray projection data by performing the X-ray imaging of the subject P. For example, the imager 120 is used while accommodated in an X-ray protective chamber 146. The image processing apparatus 180 processes the X-ray projection data collected by the imager 120, and generates various X-ray images (specifically, a panoramic image, a CT image, and a cephalographic image).

However, the imager 120 only needs to perform X-ray CT imaging of the subject P, and the image processing apparatus 180 processes the X-ray projection data collected by the imager 120 to generate an X-ray CT image. A configuration in which the X-ray CT imaging apparatus 110 performs CT imaging will mainly be described below.

The imager 120 includes an X-ray generator 126, an X-ray detector 128, a turning support 124, and a main body controller 150 (see FIGS. 5 and 6 to be described later, but not illustrated in FIG. 3).

The X-ray generator 126 includes an X-ray tube that is an X-ray source that emits the X-ray. An X-ray cone beam is emitted from the X-ray generator 126. The intensity (output intensity) of the X-ray cone beam is controlled by changing at least one of the tube voltage and the tube current, which are supplied to the X-ray generator 126. The X-ray generator 126 (particularly, at least one of tube voltage and tube current) is controlled by an X-ray generator drive controller 152h of the main body controller 150.

An X-ray cone beam shape adjuster 127 is provided on the side irradiated with the X-ray cone beam with respect to the X-ray generator 126. The X-ray generator 126 and the X-ray cone beam shape adjuster 127 are supported by one end of the turning support 124.

The X-ray cone beam shape adjuster 127 controls spread of the X-ray cone beam emitted from the X-ray generator 126, and adjusts the X-ray cone beam into a shape according to the imaging purpose. For example, the X-ray cone beam shape adjuster 127 is a member in which an X-ray controlling hole is made, and permits the passage of part of the X-ray generated from the X-ray generator 126 while shielding the outside of the passing range according to the shape and size of the X-ray controlling hole. Consequently, the range of the X-ray cone beam traveling to the X-ray detector 128 is controlled. For example, the X-ray cone beam shape adjuster 127 switches a plurality of types of X-ray controlling holes made to control the X-ray, or moves the member constituting the X-ray controlling hole to adjust an opening width of the X-ray regulating hole, thereby adjusting an amount of the shielded X-ray in the X-rays generated from the X-ray generator 126, namely, a control amount. The X-ray cone beam shape adjuster 127 is controlled by the X-ray generator drive controller 152h.

The X-ray detector 128 detects the X-ray cone beam emitted from the X-ray generator 126. The X-ray detector 128 may be constructed with a flat panel detector (FPD) including a detection surface spreading flat or an image intensifier (I.I.).

A plurality of detecting elements arranged on the detection surface of the X-ray detector 128 convert the intensity of the incident X-ray into an electric signal. The electric signal is input to the main body controller 150 or the image processing apparatus 180 as an output signal, and an X-ray projection image is generated based on the output signal.

The X-ray detector 128 is supported by the other end of the turning support 124 so as to be opposed to the X-ray generator 126 with a space between the X-ray detector 128 and the X-ray generator 126. The detection surface of the X-ray detector 128 is irradiated with the X-ray cone beam emitted from the X-ray generator 126.

The turning support 124 is suspended from a horizontal arm 123 with a rotation shaft 125 with interposed therebetween. The turning support 124 extends in the horizontal direction while being suspended. A casing 124a is attached to one end of the turning support 124, and a casing 124b is attached to the other end of the turning support 124. The X-ray generator 126 and the X-ray cone beam shape adjuster 127 are supported while accommodated in the casing 124a. The X-ray generator 126 emits the X-ray cone beam from one end to the other end of the turning support 124. The X-ray detector 128 is accommodated in the casing 124b while the X-ray detection surface of the X-ray detector 128 is oriented toward the side of the X-ray generator 126. Consequently, the turning support 124 supports the X-ray generator 126 at one end of the turning support 124, and supports the X-ray detector 128 at the other end of the turning support 124.

The turning support 124 is supported via a support column 121 and a horizontal arm 123.

The support column 121 is supported in a vertical attitude on a base 121B placed on a floor surface or the like. An elevating unit 122 is provided on the support column 121 so as to be elevated. The elevating unit 122 is elevated by an elevation drive mechanism. A linear actuator such as a moving mechanism including a ball screw mechanism and a motor or a linear motor is used as the elevation drive mechanism, and the elevation drive mechanism is incorporated in the support column 121 to elevate the elevating unit 122. The horizontal arm 123 is supported by the elevating unit 122 so as to extend in a horizontal direction. A turning drive mechanism 130 is incorporated at a leading end of the horizontal arm 123.

The turning drive mechanism 130 turns the turning support 124. In this preferred embodiment, the turning drive mechanism includes a turning shaft moving mechanism 134 and a turning mechanism 132 movably supported by the turning shaft moving mechanism 134.

The turning shaft moving mechanism 134 moves the rotation shaft 125 together with the turning mechanism 132 in a direction intersecting the turning axis X1 of the rotation shaft 125 (in this case, the horizontal direction). For example, an XY table mechanism in which two linear actuators are combined in mutually orthogonal directions can be adopted as the turning shaft moving mechanism 134. The turning shaft moving mechanism 134 moves the rotation shaft 125 along the horizontal direction together with the turning mechanism 132, whereby the rotation shaft 125 can be disposed at a desired position while turning axes of the X-ray generator 126 and the X-ray detector 128 can be set at any position.

The turning mechanism 132 includes an actuator for turning-driving as the turning drive unit, specifically, a motor 132a, and is supported by the turning shaft moving mechanism 134 so as to be movable in the horizontal direction. An upper end of the rotation shaft 125 protruding upward from an intermediate portion in the extending direction of the turning support 124 is rotatably supported by the turning mechanism 132. The turning support 124 and the X-ray generator 126 and the X-ray detector 128, which are supported by the turning support 124, turn when rotation motion of the motor provided in the turning mechanism 132 is transmitted to the rotation shaft 125. The rotation motion of the motor provided in the turning mechanism 132 is transmitted to the rotation shaft 125 through a transmission mechanism such as a gear and a pulley as necessary.

In this preferred embodiment, the X-ray generator 126 and the X-ray detector 128 are attached to both ends of the U-shaped turning support 124. Alternatively, the X-ray generator 126 and the X-ray detector 128 may be supported by an annular member while opposed to each other. As to the annular member, a shaft can be provided in a support member that crosses a part of a circumferential direction or an inside of the annular member, and rotatably supported. In this preferred embodiment, the X-ray generator 126 and the X-ray detector 128 are supported so as to be rotatable around a vertical axis. Alternatively, the X-ray generator 126 and the X-ray detector 128 may be supported so as to be rotatable around an axis oblique to the vertical direction.

The turning support 124 can be elevated by the elevating unit 122 according to a height of the head P. The turning drive mechanism 130 can turn the turning support 124 such that the X-ray generator 126 and the X-ray detector 128 turn around the head P.

A head fixing device elevating unit 141A is provided on the support column 121 so as to be able to be elevated. The head fixing device elevating unit 141A is provided below the elevating unit 122. A head fixing device arm 141 extends from the head fixing device elevating unit 141A so as to extend in the same direction as the horizontal arm 123. The head fixing device arm 141 passes under the horizontal arm 123, and extends toward a lower position between the X-ray generator 126 and the X-ray detector 128. A head fixing device 142 is provided at a leading end of the head fixing device arm 141. The head fixing device 142 is located between the X-ray generator 126 and the X-ray detector 128. The head fixing device 142 includes a chin rest 142a on which a chin of the head P that is the subject can be placed and supported and a holder 142b that holds the head P that is the subject while the head P is sandwiched from both outsides. The chin of the head P is supported on the chin rest 142a and the head P is sandwiched by the holder 142b, whereby the head P is held at a given position between the X-ray generator 126 and the X-ray detector 128. The head fixing device 142 may be constructed with at least one of the chin rest 142a and the holder 142b.

A cephalogram imaging head fixing device hanging arm 143 is provided on the side opposite to the side from which the horizontal arm 123 extends from the support column 121 so as to extend in the horizontal direction, and a cephalogram imaging head fixing device 144 is supported in a suspended state by the cephalogram imaging head fixing device hanging arm 143. A cephalogram imaging X-ray detector 128b is incorporated in the cephalogram imaging head fixing device 144. A mechanism including the cephalogram imaging head fixing device hanging arm 143, the cephalogram imaging head fixing device 144, the cephalogram imaging X-ray detector 128b, and other peripheral components as necessary constitutes a cephalogram imaging X-ray detecting mechanism. A mechanism including the horizontal arm 123, the turning support 124, the casing 124*a*, the X-ray generator 126, and other peripheral components as needed during cephalogram imaging constitutes a cephalogram imaging X-ray generating mechanism. The cephalogram imaging X-ray detecting mechanism and the cephalogram imaging X-ray generating mechanism constitute a cephalogram imaging mechanism.

In this preferred embodiment, each unit for cephalogram imaging, for example, the cephalogram imaging head fixing device hanging arm 143, the cephalogram imaging head fixing device 144, and the cephalogram imaging X-ray detector 128*b* may be omitted.

The main body controller 150 including an operation panel device 158 is provided at an intermediate portion in the extending direction of the head fixing device arm 141.

In performing the X-ray imaging, the turning support 124 is stopped or rotated according to the desired imaging mode while the head P that is the subject is fixed by the head fixing device 142. In particular, the X-ray generator 126 and the X-ray detector 128 are turned around the subject P by rotating the turning support 124, which allows the obtainment of the X-ray image data necessary for the generation of the X-ray CT image and the like. In addition, panoramic photographed images can be obtained by carrying out the X-ray imaging while the turning support 124 is rotated within a certain range, which allows a panoramic image to be obtained. Additionally, the X-ray CT imaging apparatus 110 can also perform the X-ray imaging in order to obtain a cephalogram image and a pseudo-intraoral image. For example, the head P is fixed to the cephalogram imaging head fixing device 144 supported by the cephalogram imaging head fixing device hanging arm 143 extending horizontally from the support column 121 while the turning support 124 is stopped, and the X-ray is emitted from the X-ray generator 126 to perform the X-ray imaging, which allows the cephalogram image to be obtained.

The main body controller 150 is constructed with a computer, configured so as to be able to receive each instruction to the imager 120, and configured to be able to control each operation of the imager 120. The main body controller 150 is fixed to the head fixing device arm 141 extending horizontally from the support column 121. The operation panel device 158 that receives various instructions to the main body controller 150 while displaying various kinds of information from the main body controller 150 is provided in the main body controller 150. The operation panel device 158 is a touch panel including a display device such as a liquid crystal display panel and a touch detector disposed on a display screen of the display device. A touch operation of the user on the display screen is detected with the touch detector, which allows the operation on the X-ray CT imaging apparatus 110 to be received. A push button and the like may be provided near the operation panel device 158 or the like. The display device and an input device that receives the operation of the user may separately be provided.

A push button switch called a dead man switch connected to the main body controller 150 is provided on the outside of a wall of the X-ray protective chamber 146 in which the imager 120 is accommodated. The X-ray radiation is performed only while the operator depresses the dead man switch.

The image processing apparatus 180 includes an information processing main body 182 constructed with, for example, a computer or a workstation, and is connected to the imager 120 through a communication cable such that various pieces of data can be transmitted to and received from the imager 120. However, the transmission and reception of the data may be performed by wireless communication between the imager 120 and the image processing apparatus 180. The information processing main body 182 can perform various pieces of image processing based on the data transmitted from the imager 120.

A display 184*a* constructed with a display device such as a liquid crystal monitor and an operation unit 184*b* constructed with a keyboard and a mouse are connected to the image processing apparatus 180. The operator can issue various commands to the information processing main body 182 by operating a pointer through the mouse or on characters or images displayed on the display 184*a*. The display 184*a* may be constructed with a touch panel.

A part or all of the pieces of processing of the image processing apparatus 180 may be performed by the main body controller 150. Alternatively, a part or all of the pieces of processing of the main body controller 150 may be performed by the image processing apparatus 180. That is, each piece of processing of the main body controller 150 and the image processing apparatus 180 may be performed by a single computer provided at any place, or a plurality of processors provided at any place in a distributed manner.

<Block Diagram of X-Ray CT Imaging Apparatus>

Figure 5:
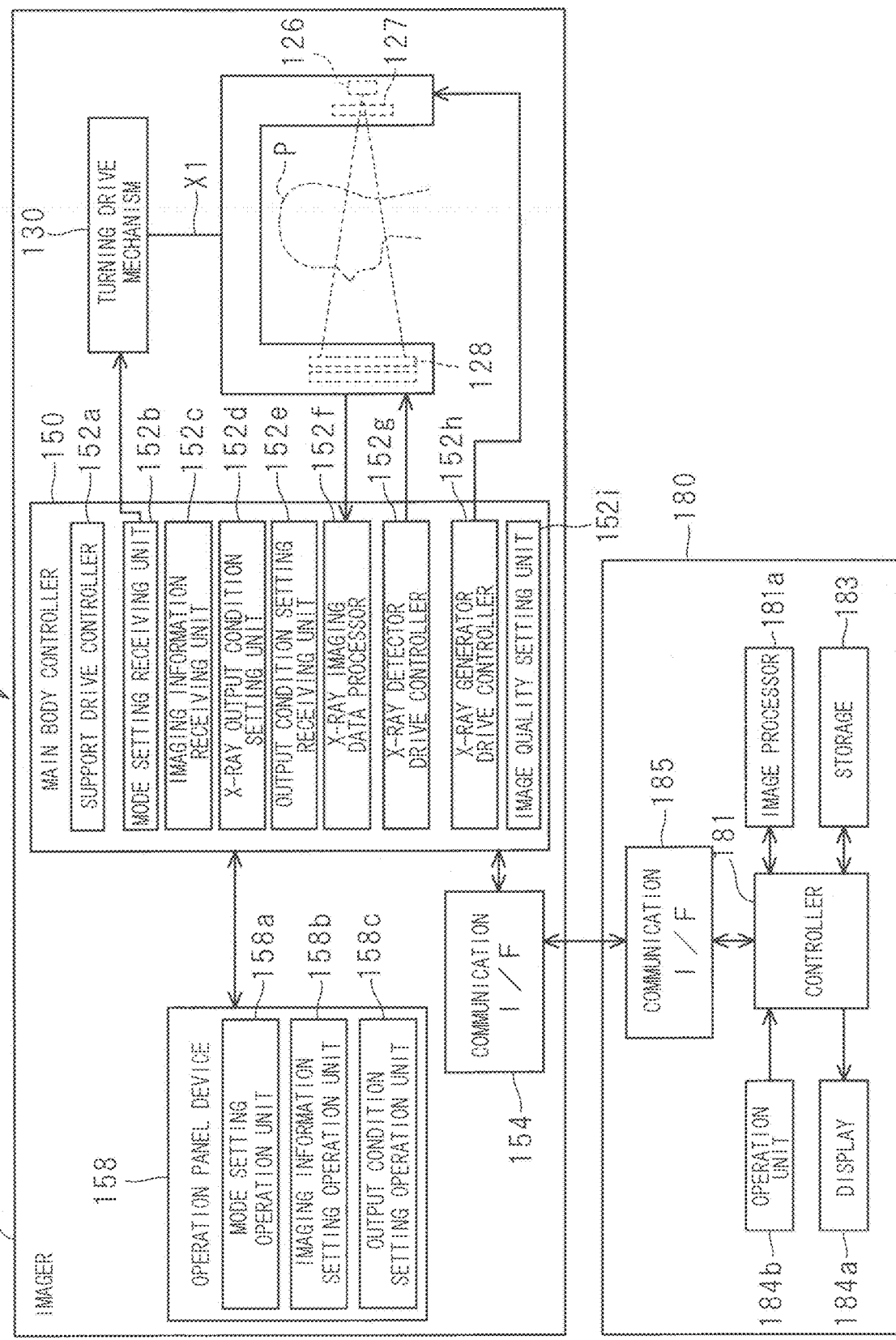
FIG. 5 is a functional block diagram of the X-ray CT imaging apparatus.

FIG. 5 is a functional block diagram of the X-ray CT imaging apparatus 110, and FIG. 6 is a block diagram illustrating an electrical configuration of the main body controller 150.

The main body controller 150 controls an X-ray imaging operation of the imager 120, and is constructed with a computer as an example of the processor where a central processing unit (CPU) 150*a*, a random access memory (RAM) 150*b*, a storage 150*c*, an input and output unit 150*d*, an operation input unit 150*e*, and an image output unit 150*f* are mutually connected through a bus line 150*g* (see FIG. 6). The storage 150*c* is constructed with a non transitory computer readable medium such as a flash memory or a hard disk device, and stores an imaging program 151 that receives various instructions relating to the X-ray imaging through the operation panel device 158 and controls the operation when the imager 120 performs the X-ray CT imaging according to the various instructions. The imaging program 151 includes an X-ray CT imaging condition setting program 151*a* that automatically sets the output condition of the X-ray generator 126 according to the setting relating to the X-ray imaging when the setting relating to the X-ray imaging is received through the operation panel device 158.

A reference table 152 in which the output condition of the X-ray generator 126 is correlated with the setting relating to the X-ray imaging is stored in the storage unit 150*c*. An example of the reference table 152 will be described later.

The RAM 150*b* serves as a work area when the CPU 150*a* performs predetermined processing. The input and output unit 150*d* is connected to a motor included in the turning drive mechanism 130 of the imager 120, the X-ray generator 126, the X-ray detector 128, and the like. The operation input unit 150*e* is connected to the touch detector of the operation panel device 158, and the image output unit 150*f* is connected to the display of the operation panel device 158.

In the main body controller 150, the CPU 150*a* performs processing according to a procedure described in the imaging program 151 and an instruction received through the operation panel device 158, whereby the display on the operation panel device 158 is controlled while various settings relating to the imaging are received. The CPU 150*a* performs the processing according to the procedure described in the imaging program 151 and the received various instructions relating to the imaging, thereby controlling the drive of the turning drive mechanism 130, the X-ray generator 126, the X-ray detector 128, and the like. Consequently, the X-ray generator 126 and the X-ray detector 128 turn around the subject P, and the X-ray cone beam emitted from the X-ray generator 126 passes through the subject P to enter the X-ray detector 128. The X-ray CT image can be generated based on the data detected by the X-ray detector 128.

As illustrated in FIG. 5, the main body controller 150 includes a support drive controller 152a, a mode setting receiving unit 152b, an imaging information receiving unit 152c, an X-ray output condition setting unit 152d, an output condition setting receiving unit 152e, an X-ray imaging data processor 152f, an X-ray detector drive controller 152g, an X-ray generator drive controller 152h, and an image quality setting unit 152i. Each controller is a function implemented by the operation of the CPU (general-purpose circuit) according to the imaging program 151. A part or all of the functions may be implemented in a hardware manner by construction of a dedicated circuit. Each of the functions may be processed in a distributed manner by a plurality of computers. A mechanical entity of a function realized by the CPU operating according to an electrical signal as a program is a program and a circuit which functions by the program.

The support drive controller 152a controls the turning of the turning support 124 by controlling the turning drive mechanism 130. Specifically, in performing the X-ray CT imaging, the support drive controller 152a rotates the X-ray generator 126 and the X-ray detector 128, which are supported by the turning support 124, around the rotation axis X, thereby turning the X-ray generator 126 and the X-ray detector 128 around the subject P. According to the output condition set by the X-ray output condition setting unit 152d (to be described later), the support drive controller 152a can control the speed at which the X-ray generator 126 and the X-ray detector 128 are turned and the turning range (turning angle).

The mode setting receiving unit 152b receives the settings of a low dose mode and a high resolution mode through the operation panel device 158. The low dose mode is a mode in which the X-ray CT imaging with a low dose is performed according to at least one of the size of the imaging area, the imaging purpose, and the imaging region in some imaging area cases as described later. That is, as described later, the X-ray CT imaging apparatus 110 can perform the X-ray CT imaging with the low dose and the high-resolution X-ray CT imaging. The X-ray CT imaging with the low dose is the imaging in which the X-ray CT imaging is performed while the dose of the X-ray emitted from the X-ray generator 126 is suppressed. The high resolution mode is a mode for performing high resolution X-ray CT imaging. In the X-ray CT imaging with the low dose, the dose for the subject P is decreased while a noise is easily included. The high-resolution X-ray CT imaging is the imaging in which the X-ray CT imaging is performed with the dose higher than that of the case of the X-ray CT imaging with the low dose. In the high-resolution X-ray CT imaging, the dose for the subject P is increased while the sharp X-ray CT image can be obtained with a less noise. The output condition of the X-ray detector 128 is set according to each of the low dose mode and the high resolution mode. For example, the setting is defined in the reference table 152. This point will be described later. A low resolution mode is a specific example of the regular observation CT imaging mode and the high resolution mode is a specific example of the detailed observation CT imaging mode.

In the X-ray CT imaging apparatus 110, switching between the low dose mode and the high resolution mode is not indispensable. For example, only the low dose mode may be performed.

The imaging information receiving unit 152c receives imaging information about at least one of the size of the imaging area, the imaging purpose, and the imaging region through the operation panel device 158. Contents of the imaging information include at least one of the size of the imaging area, the imaging purpose, and the imaging region. Reception is made by input, for example. In this preferred embodiment, an example in which the imaging information receiving unit 152c receives the size of the imaging area and the imaging region through the operation panel device 158 will be described. An example in which the imaging information receiving unit 152c receives the imaging purpose will be described in a later modification.

At this point, the imaging information receiving unit 152c also receives the setting of the physique through the operation panel device 158. More specifically, the imaging information receiving unit 152c receives the setting whether the subject has the physique of the child or the physique exceeding the child as the setting of the physique.

The X-ray output condition setting unit 152d sets the X-ray output condition according to at least one of the size of the imaging area, the imaging purpose, and the imaging region, which are received by the imaging information receiving unit 152c. In this preferred embodiment, an example in which the imaging information receiving unit 152c sets the X-ray output condition according to the size of the imaging area will be described. An example in which the X-ray output condition setting unit 152d sets the X-ray output condition according to the imaging purpose and the imaging region will be described in the later modification.

At this point, in addition to the setting of the imaging area relating to at least one of the size of the imaging area, the imaging purpose and the imaging region, which are received by the imaging information receiving unit 152c, the X-ray output condition setting unit 152d automatically sets the output condition of the X-ray generator 126 according to the setting of the physique, more specifically the setting whether the subject has the physique of the child or the physique exceeding the child. In the case that the output condition is manually set in the output condition setting receiving unit 152e, the output condition setting receiving unit 152e changes the automatically-set output condition according to a content of the manual setting.

The output condition setting receiving unit 152e receives the operator's manual setting relating to the output condition of the X-ray generator 126 through the operation panel device 158. That is, in the case that the operator wants to appropriately change and adjust the output condition with respect to the output condition automatically set by the X-ray output condition setting unit 152d, the operator can change the automatically-set output condition through the operation panel device 158.

The manual setting function for the automatically-set output condition may be omitted.

The X-ray imaging data processor 152f performs image processing such as noise reduction processing on the data detected by the X-ray detector 128. A median filter with a value of each pixel as a median value of surrounding pixels, and a moving average filter with the value of each pixel as an average value of surrounding pixels can be adopted as the noise reduction processing.

The X-ray detector drive controller 152g controls drive of the X-ray detector 128. The X-ray detector drive controller 152g may control on and off of a binning function of collecting the plurality of pixels of the X-ray detector 128 as one pixel and a unit of the pixels collected by the binning function.

The X-ray generator drive controller 152h controls on and off of the X-ray generator 126 while controlling at least one of the tube voltage and the tube current of the X-ray generator 126 according to the X-ray output condition automatically set by the X-ray output condition setting unit 152d.

The image quality setting unit 152i automatically sets the image quality of the X-ray CT image according to at least one of the setting of the imaging area received by the imaging information receiving unit 152c and the output condition of the X-ray generator 126 automatically set by the X-ray output condition setting unit 152d. At this point, the image quality setting unit 152i automatically sets the image quality of the X-ray CT image by adjusting a voxel size when the X-ray CT image is reconstructed based on the image obtained by the X-ray detector 128. For example, in the output condition, there are a first dose and a second dose, if the first dose is in a relationship greater than the second dose, setting the first dose is the first output condition, and setting the second output condition is the second dose, in the case that the second output condition is automatically set, the noise is easily included, so that the voxel size is set relatively large in order to eliminate the influence of the noise as much as possible. Further, for example, in the case that the first output condition is automatically set, the noise is hardly included, so that the voxel size is set smaller than that of the above case to obtain the sharp image with the high resolution. Further, for example, the voxel size may be set relatively large in the case that the relatively wide imaging area E2 wider than the relatively narrow imaging area E1 is imaged under the second output condition.

The image quality setting unit 152i may automatically set the image quality of the X-ray CT image according to the received setting information of the imaging area irrespective of the output condition of the X-ray generator 126 that has been set. For example, reduction in the voxel size when there is acceptance for the above-mentioned detailed observation purpose, and increase in the voxel size when receiving the above-mentioned regular observation purpose are possible. The voxel size may be reduced when there is acceptance of a relatively narrow imaging area of the first spread and the voxel size may be increased when there is reception of a relatively wide imaging area of the second spread.

The setting value (for example, a voxel value) in the image quality setting unit 152i is given to the image processing apparatus 180. The image processing apparatus 180 reconstructs the X-ray CT image based on the set voxel value. That is, three-dimensional data is generated based on the data detected by the X-ray detector 128, and a tomographic image is cut out from the three-dimensional data to generate the X-ray CT image. The voxel value is a three-dimensional unit in generating the three-dimensional data.

The setting of the image quality by the image quality setting unit 152i is not limited to the above example. A role of the image quality setting unit 152i is to exclude the influence of the noise as much as possible because the noise is easily included when the output condition with the relatively small dose is automatically set. Conversely, in the case that the output condition with the relatively large dose is automatically set, a boundary is relatively clear and the data with less noise can be obtained, so that a degree of the image quality adjustment is preferably small although such the image quality adjustment that the noise is reduced is unnecessary.

Processing different from the adjustment of the voxel size can be adopted as the image quality setting processing by the image quality setting unit 152i.

For example, the image quality setting unit 152i may control on and off of the binning function of the X-ray detector 128 or adjust the unit of collected pixels by the binning function. For example, the binning function may be turned on in the case that the output condition with the relatively small dose is automatically set, and the binning function may be turned off in the case that the output condition with the relatively large dose is automatically set. For example, the unit of the pixels that are collected by the binning function in the case that the output condition with the relatively small dose is automatically set may be larger than the unit of the pixels that are collected by the binning function in the case that the output condition with the relatively large dose is automatically set. Turning on the off state of the binning function or making the pixel unit gathered by the binning function larger is called high binning.

The image quality setting unit 152i may set the image quality by adjusting detection sensitivity of the X-ray detector 128. For example, the detection sensitivity may be increased in the case that the output condition with the relatively small dose is automatically set, and the detection sensitivity may be decreased in the case that the output condition with the relatively large dose is automatically set. As a specific example, capacitor elements (capacitors) that receive pixel signals of the detection surface are capacitively prepared as plural types or variably prepared so that they can be switched or changed, and when the output condition where the dose is relatively small is automatically set, the capacity is decreased, and when the output condition having the relatively large dose is automatically set, the capacity is increased. The evaluation of the strength of the signal in the capacity is carried out in multiple steps (the same number of steps common to each capacity, for example 16 bits are possible).

The image quality setting unit 152i may adjust a slice thickness in reconstructing the X-ray CT image. That is, the three-dimensional data is generated based on the data detected by the X-ray detector 128, a slice is cut out from the three-dimensional data, and the X-ray CT image is generated based on one slice or a plurality of overlapped slices. The increase in slice thickness contributes to the noise reduction leading to averaging of values in a thickness direction. For this reason, the slice thickness is set large in the case that the output condition with the relatively small dose is automatically set, and the slice thickness is set small in the case that the output condition with the relatively large dose is automatically set. The automatically-set value of the slice thickness is given to the image processing apparatus 180. The image processing apparatus 180 reconstructs the X-ray CT image based on the set slice thickness.

Further, whether the noise reduction processing such as a smoothing arithmetic filter including a median filter and a moving average filter which is performed on at least one of the data obtained by the X-ray detector 128, the three-dimensional image based on the data, and the X-ray CT image may be adjusted. For example, the noise reduction processing is performed in the case that the output condition with the relatively small dose is automatically set, and the noise reduction processing is not performed in the case that the output condition with the relatively large dose is automatically set. Strength of the noise processing may be changed between the two. Necessity of performing the noise processing and a selection instruction are given from the main body controller 150 to the image processing apparatus 180.

When performing the above pieces of processing, particularly when performing the pieces of processing as the mode setting receiving unit 152b, the X-ray output condition setting unit 152d, and the output condition setting receiving unit 152e, the main body controller 150 receives the touch operation on the operation panel device 158 while controlling the display content of the operation panel device 158. In this point, the operation panel device 158 acts as a mode setting operation unit 158a that performs the setting operation on the mode setting receiving unit 152b, an imaging information setting operation unit 158b that performs the setting operation on the X-ray output condition setting unit 152d, and an output condition setting operation unit 158c that performs the setting operation on the output condition setting receiving unit 152e.

Here, the process of increasing the voxel size, the noise reduction process by the filter or the like, the binning process, the process of increasing the slice thickness, etc. are the processes in the direction of combining the signal of one pixel and the signal of the neighboring pixel, and is referred to as pixel signal combining type processing.

Among them, signal processing on the X-ray detector side, such as binning switching of the X-ray detector 128, is referred to as pixel signal combination type detection signal processing, and image processing on the image processing apparatus side, such as processing for increasing slice thickness is referred to as pixel signal combining type image processing.

As an example of control, the following control can be considered. The first imaging area and the second imaging area are considered as an imaging target area. When comparing the area, the first imaging area is narrower and the second imaging area is wider. X-ray CT imaging is performed on the first imaging area under the first output condition and the second imaging area under the second output condition. The first output condition and the second output condition are set by the X-ray output condition setting unit 152d, the dose in the first output condition is the first dose, and the dose in the second output condition is the second dose. When comparing the sizes, the first dose is larger and the second dose is smaller.

First projection image data is obtained by X-ray CT imaging of the first imaging area, and second projection image data is obtained by X-ray CT imaging of the second imaging area.

And the image quality setting unit 152i sets the image quality of the X-ray CT image to be produced. For example, high binning is performed for X-ray CT imaging of the second imaging area, and the pixel signal combining type processing is performed on the second projection image data.

The main body controller 150 is communicably connected to the image processing apparatus 180 through a communication interface (I/F) 154.

The image processing apparatus 180 is constructed with a computer or a workstation. That is, the image processing apparatus 180 includes a CPU that an example of a processor that performs various pieces of processing, a ROM that is a read-only memory in which a basic program is stored, and a RAM that is a readable and writable memory in which various pieces of information are stored. The CPU functions as a controller 181 by operating according to the control program. The controller 181 is connected to an image processor 181a and a storage 183. The image processor 181a processes the X-ray transmission image, which is generated based on the signal output by the X-ray detector 128 when the imager 120 performs the X-ray CT imaging, and generate the X-ray CT image. The storage 183 stores an application or data.

The image processor 181a is a function implemented by an image processing processor. The image processor 181a is a function implemented by the operation of the CPU of the controller 181 according to an application program.

For example, in the case that the imager 120 performs the X-ray CT imaging, the image processor 181a generates the three-dimensional image by performing predetermined pre-processing, filtering, and back-projection processing on the plurality of acquired projection images, and generates the CT image of each section obtained by slicing the imaging area based on the three-dimensional image.

For example, a plurality of projection images obtained by X-ray CT imaging are processed as frame data, three-dimensional mesh data composed of three-dimensional voxel data (three-dimensional pixels in image processing) is constructed, and slice data cut from three-dimensional mesh data is subjected to visualization process into tomographic images, or the three-dimensional mesh data is subjected to visualization process into volume rendering images. In this manner, an X-ray CT image is produced.

The display 184a that displays the images indicating various pieces of information and the operation unit 184b with which the operator performs an input operation are connected to the controller 181. The image processing apparatus 180 is communicably connected to the main body controller 150 through communication I/F 185.

<Various Setting Examples>

An example in which the main body controller 150 receives various settings through the operation panel device 158 will be described.

Figure 7:
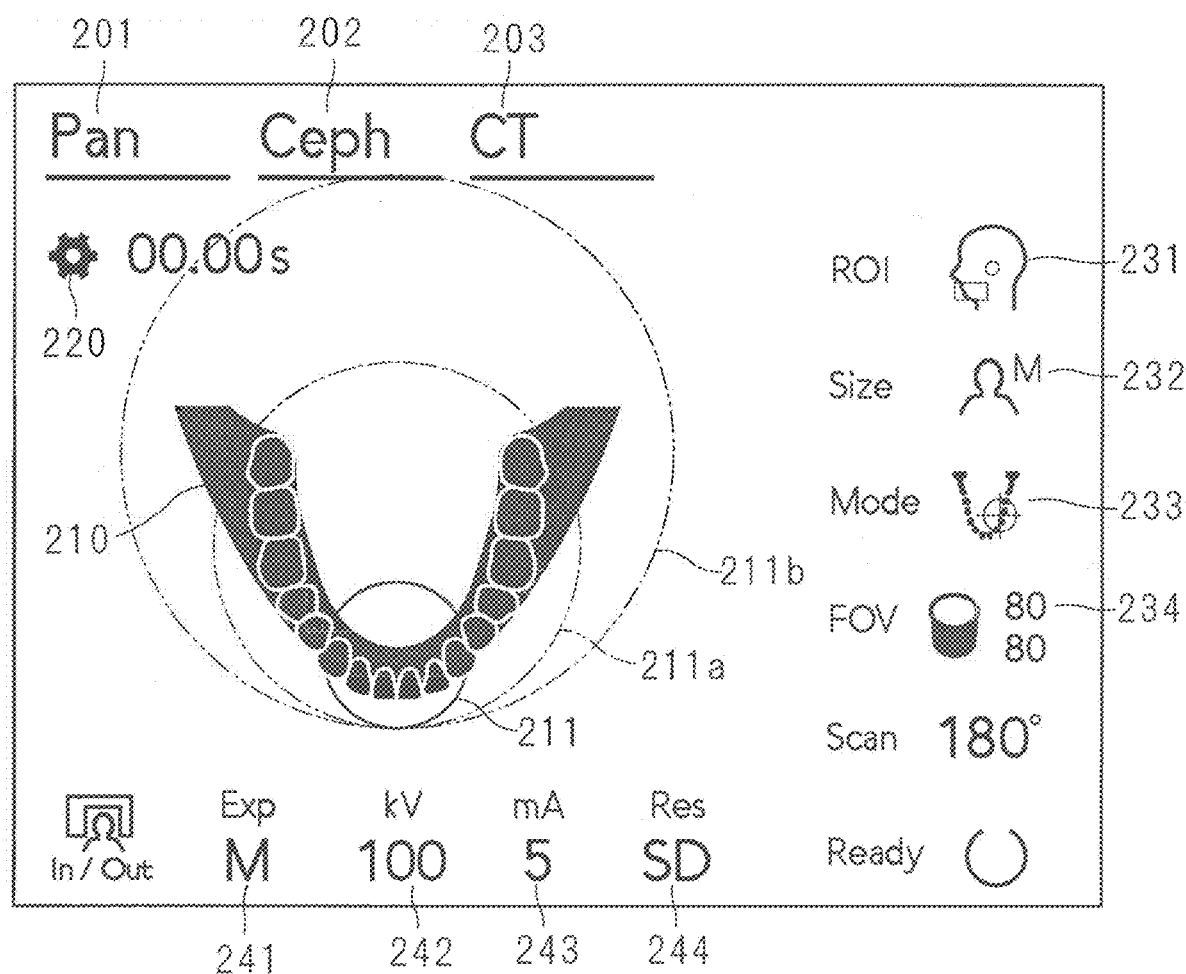
FIG. 7 is a view illustrating a display example of an operation panel device.

FIG. 7 is a view illustrating a display example of the operation panel device 158.

As illustrated in FIG. 7, imaging mode selection images 201, 202, 203 corresponding to a plurality of X-ray imaging modes are displayed on the operation panel device 158. In this case, the imaging mode selection images 201, 202, 203 are displayed in an upper portion of the display area of the operation panel device 158.

More specifically, the imaging mode selection images 201, 202, 203 include the panoramic imaging mode selection image 201 corresponding to the panoramic imaging mode, the cephalogram imaging mode selection image 202 corresponding to the cephalogram imaging mode, and the CT imaging mode selection image 203 corresponding to the CT imaging mode.

As used herein, the panoramic imaging mode is an imaging mode performed to obtain one image of the entire mouth (or part of the mouth) along the row of teeth, and is a mode in which the X-ray imaging is performed while, for example, the turning support 124 is rotate within a predetermined range. An image representing a character "Pan" is displayed as the panoramic imaging mode selection image 201. The X-ray generator 126 and the X-ray detector 128 are used in the panoramic imaging mode.

The cephalogram imaging mode is an imaging mode in which head X-ray standard photograph imaging, namely, cephalogram imaging is performed, and is a mode in which the X-ray imaging is performed on the head while, for example, the rotation of the turning support 124 is stopped. An image representing a character "Ceph" is displayed as the cephalogram imaging mode selection image 202. The cephalogram imaging mechanism is used in the head X-ray standard photograph imaging.

The CT imaging mode is an imaging mode performed to obtain the tomographic image of the entire row of teeth (or a part of the row of teeth), and is a mode in which the X-ray imaging is performed while, for example, the turning support 124 is rotated. An image representing a character "CT" is displayed as the CT imaging mode selection image 203. The X-ray generator 126 and the X-ray detector 128 are used in the CT imaging mode.

The images displayed as the imaging mode selection images 201, 202, 203 are not limited to the above example. For example, the images displayed as the imaging mode selection images 201, 202, 203 may be an illustration in which each imaging mode is imaged.

In the display screen of the operation panel device 158, the touch detector is provided as a two-dimensional position detector that detects a touch position with respect to a display outer surface. When a user touches any one of the imaging mode selection images 201, 202, 203, the touch detector receives a selection operation for any one of the imaging mode selection images 201, 203, 203. When the selection operation is received, one imaging mode selection image corresponding to the selection operation may visually be displayed so as to be distinguishable from other imaging area selection images. Consequently, the selection of the imaging mode is received in the main body controller 150. When the selection operation for one of the imaging mode selection images 201, 203, 203 is received, selected one of the imaging mode selection images 201, 203, 203 may be displayed in a color different from others (including a different shade of the color) so as to be distinguishable from others.

An imaging position designating image 210 is displayed on the operation panel device 158. In this case, an image indicating the dental arch is displayed as the imaging position designating image 210. The imaging position designating image 210 is largely displayed in a central portion of the display screen of the operation panel device 158. The imaging position designating image may be an X-ray image, for example, the cephalogram image obtained by separately imaging an examinee on whom the X-ray imaging is actually performed. An image 211 (in this case, a circle) indicating the imaging position is displayed while superposed on the imaging position designating image 210. The image 211 indicates the imaging position in the imaging position designating image 210. It may be considered that the imaging position designating image 210 and the image 211 indicating the imaging position constitute an imaging position setting scout image.

Three sizes of images 211, 211*a*, 211*b* are illustrated in FIG. 7. The image 211 having the smallest circle indicates an area where the imaging is performed on a part of the dental arch (about five or six teeth on a front tooth side and two or three teeth on a molar tooth side). The image 211*a* having an intermediate circle indicates an area where the imaging is performed on the entire dental arch. The image 211*b* having the largest circle indicates an area where the imaging is performed on the entire maxillofacial area (it may be an area including all the left and right teeth extending from the front tooth to the molar and both the temporomandibular joints). One image having a size corresponding to the setting by a imaging area setting image 234 (to be described later) is displayed as the images 211, 211*a*, 211*b*.

The user touches the position where the imaging is desired with respect to the imaging position designating image 210, thereby receiving the setting of the imaging position in the imaging position designating image 210. Alternatively, the setting of the imaging position may be performed using a direction key or the like.

Figure 8:
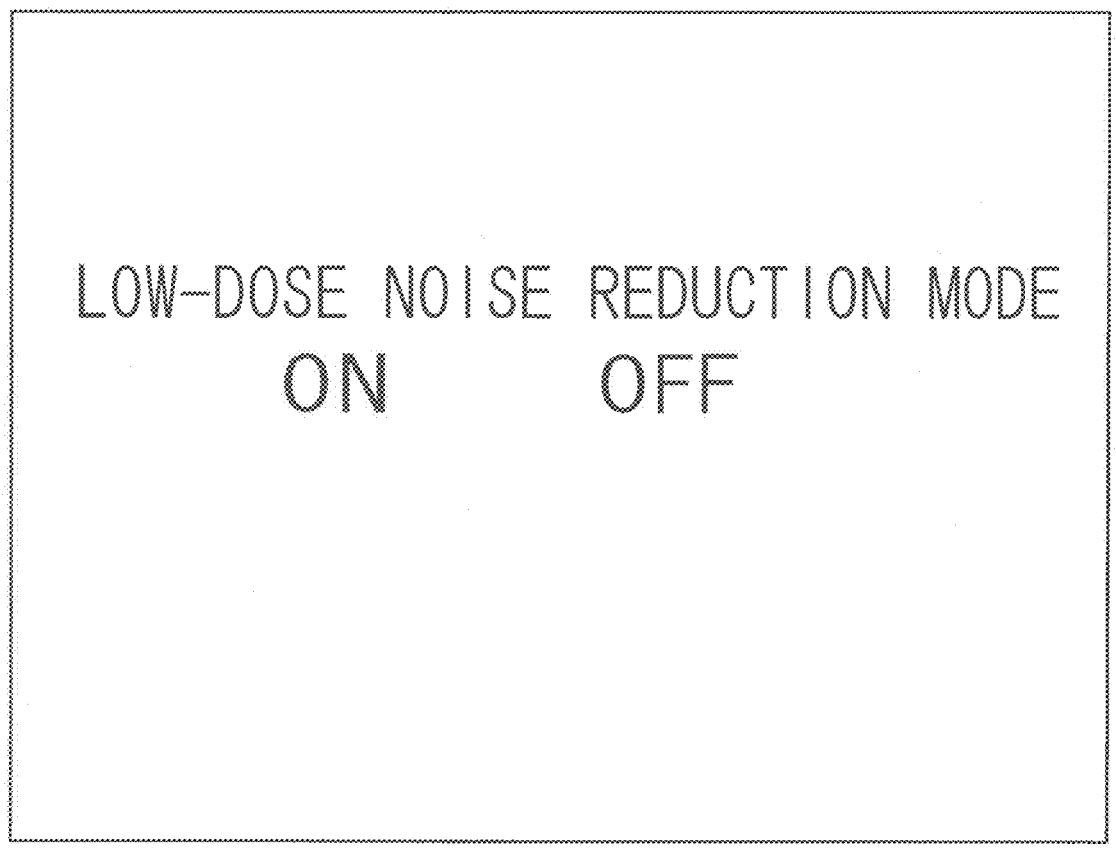
FIG. 8 is a view illustrating a setting display example of the operation panel device.

A radiation mode setting image 220 for setting a radiation mode is displayed on the operation panel device 158. In this case, the radiation mode setting image 220 is an image imitating a gear, and is displayed below the imaging mode selection image 201. When the user touches the radiation mode setting image 220, characters of "low-dose noise reduction mode", "ON", "OFF" are displayed as illustrated in FIG. 8. When the user touches the character "ON", the "low-dose noise reduction mode" is turned on and the setting of the low dose mode is received. When the user touches the character "OFF", the setting of the high resolution mode is received. After a predetermined time elapses since the setting, or another area (for example, the low-dose noise reduction mode) is touched, which allows the display screen to be turned to the original display screen. By turning on the low-dose noise reduction mode, the low dose mode can be selected, and the noise reduction processing is performed such that strong noises is not included even if the X-ray CT imaging is performed with the low dose.

In the operation panel device 158, a region-of-interest setting image 231, a patient size selection image 232, a CT imaging position attached mode selection image 233, an imaging area setting image 234, and a scan mode selection image 235 are displayed as the imaging condition setting images corresponding to the CT imaging mode. In the first preferred embodiment, the images 231, 232, 233, 234, 235 are displayed in the area on the right side of the display screen of the operation panel device 158. The presence or absence of display of other images 232, 233, 234, 235 may be changed or other images 232, 233, 234, 235 may be changed to another image according to a setting content of the region-of-interest setting image 231.

Figure 9:
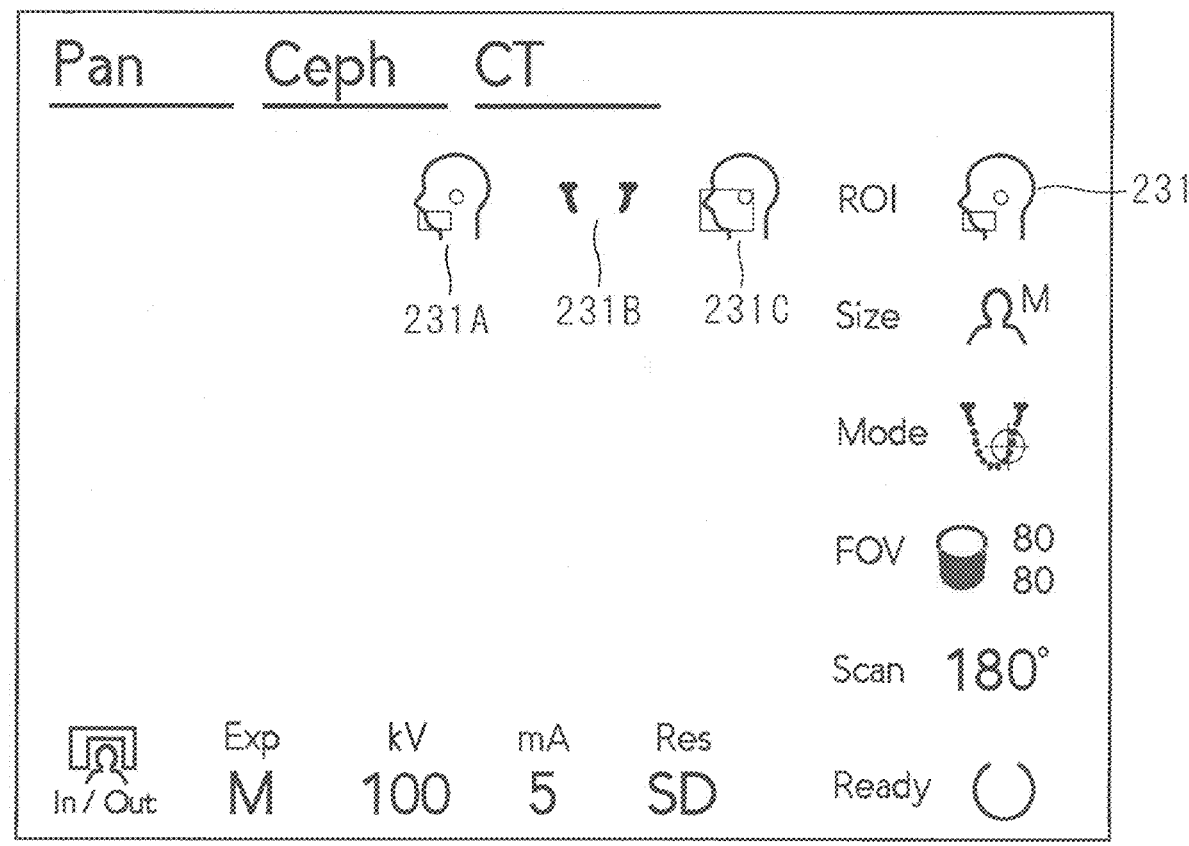
FIG. 9 is a view illustrating a setting display example of the operation panel device.

The region-of-interest setting image 231 is an image in which an illustration image of the region of interest is added beside a character "ROI". The user can set the region of interest (ROI) through the region-of-interest setting image 231. When the user touches the region-of-interest setting image 231, a plurality of region-of-interest setting images 231A, 231B, 231C are displayed as illustrated in FIG. 9. The plurality of region-of-interest setting images 231A, 231B, 231C include a tooth row setting image 231A in which the dental arch is set to the region of interest, a temporomandibular joint setting image 231B in which the temporomandibular joint is set to the region of interest, and a maxillofacial setting image 231C in which the maxillofacial area is set to the region of interest. When the user touches any one of the region-of-interest setting images 231A, 231B, 231C while the images 231A, 231B, 231C are displayed side by side, thereby receiving the setting of the region of interest. The displayed content of the imaging area setting image 234 (to be described later) changes depending on the selection of one of the region-of-interest setting images 231A, 231B, 231C.

Figure 10:
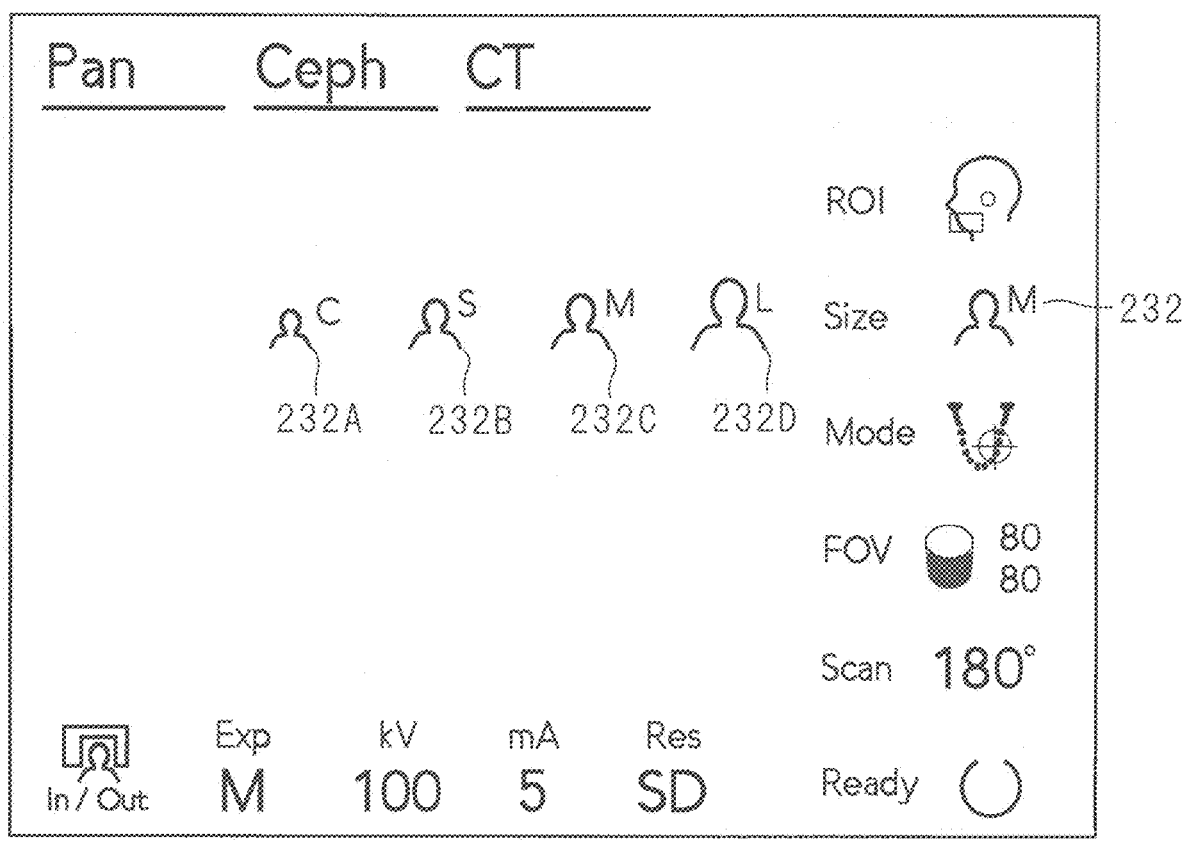
FIG. 10 is a view illustrating a setting display example of the operation panel device.

The patient size setting image 232 is an image used to set the physique, and is an image in which an illustration image illustrating an upper half of the body and a character (in this case, "M") indicating the size are added beside a character "Size". The user can set the patient size (physique) through the patient size setting image 232. When the user touches the patient size setting image 232, a plurality of patient size selection images 232A, 232B, 232C, 232D are displayed as illustrated in FIG. 10. The plurality of patient size selection images 232A, 232B, 232C, 232D include a plurality of patient size display illustration images representing upper body contours having sizes different from one another. More specifically, the patient size selection image 232A is an image in which "c" (an initial letter of the child) is added to the smallest patient size display illustration image, the patient size selection image 232B is an image in which "S" (an initial letter of small) is added to the second smallest patient size selection image, the patient size selection image 232C is an image in which "M" (an initial letter of middle) is added to the third smallest patient size selection image, and the patient size selection image 232D is an image in which "L" (an initial letter of large) is added to the largest patient size selection image. The user touches one of the images 232A, 232B, 232C, 232D while the images 232A, 232B, 232C, 232D are displayed side by side, thereby receiving the setting of the patient size (physique). In particular, the setting that the physique is the child is received when the patient size selection image 232A is selected, and the setting that the physique exceeds the child is received when the patient size selection images 232B, 232C, and 232D are selected.

The CT imaging position attached mode selection image 233 is an image used to change the mode performing the position setting. By operating the CT imaging position attached mode selection image 233, the imaging area based on the panoramic image or the two-direction scout image can be set in addition to the setting of the imaging position of the dental arch.

Figure 11:
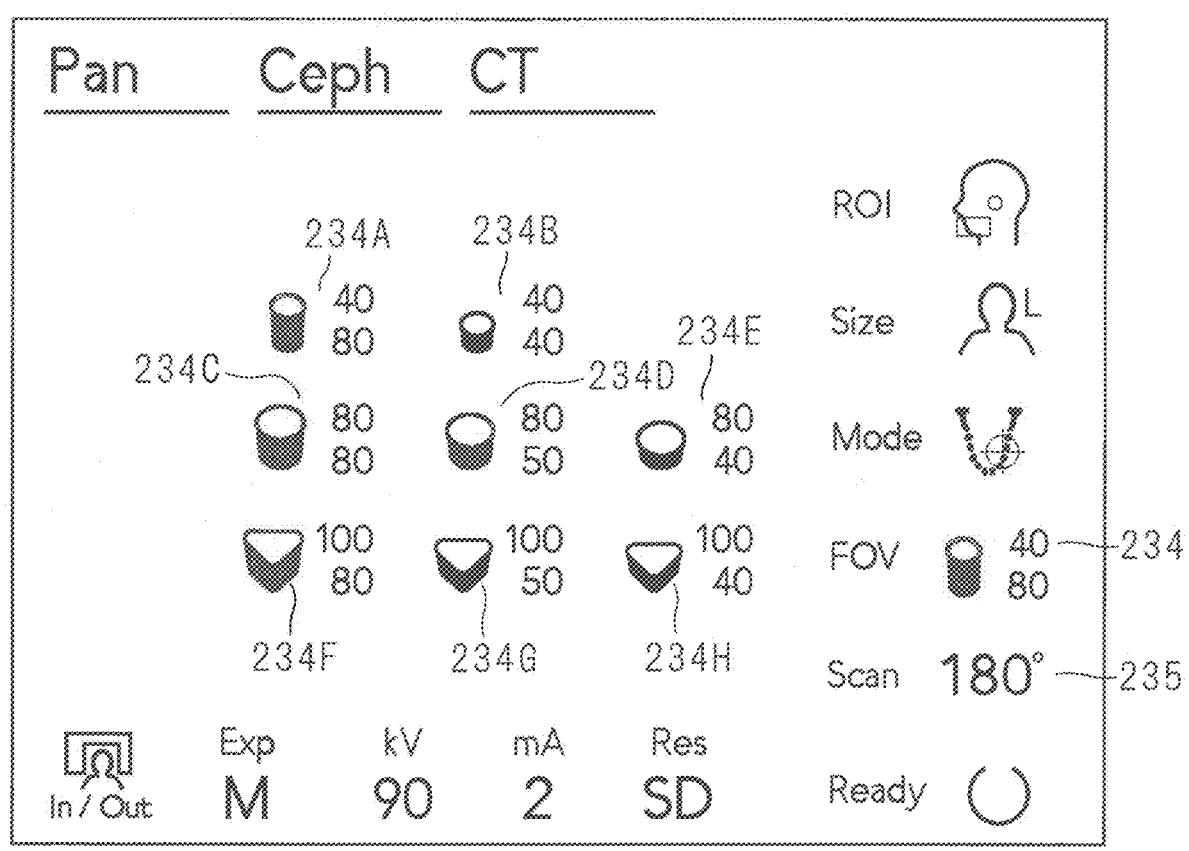
FIG. 11 is a view illustrating a setting display example of the operation panel device.

The imaging area setting image 234 is an image used to set the size of the imaging area. In this case, the imaging area setting image 234 is an image in which an image of a numerical value (such as a diameter and a height) representing the size of the imaging area is added to an illustration (for example, a columnar shape) three-dimensionally representing the shape of the imaging area. When the user touches the imaging area setting image 234, a plurality of imaging area setting images 234A to 234H are displayed as illustrated in FIG. 11. The imaging area setting images 234A to 234H are a plurality of CT imaging area candidate images representing CT imaging area sizes different from one another. That is, the imaging area setting images 234A to 234H are used to set the CT imaging area in which one of the diameter, the height, and the imaging area shape is different. The display examples of the imaging area setting images 234A to 234H in FIG. 11 are display examples of the case that the tooth row setting image 231A is selected from the region-of-interest setting image 231. For example, when the maxillofacial setting image 231C is selected in the region-of-interest setting image 231, the number of imaging area setting images 234 may be decreased, only one setting obtained by the imaging of the maxillofacial area may be made with respect to an extent of the region of interest, and only the height of the region of interest may be varied. Assuming the size of typical tooth jaw, the relatively narrow imaging area setting images 234A, 234B are an image that are aimed at the range of the diameter of 40 mm to perform the selection and designation of a local CT imaging mode in which about three teeth can be imaged. The relatively wide imaging area setting images 234C, 234D, 234E are an image that are aimed at the range of the diameter of about 80 mm to perform the selection and designation of the CT imaging mode for almost a whole of the tooth jaw. The imaging area setting image 234F, 234G, 234H used to perform the selection and designation of the wide area setting screen CT imaging mode are an image used to perform the selection and designation of the imaging area targeting the entire jaw including the molar by forming the imaging area into a triangular shape with rounded corners. The setting of the CT imaging area size is received when the user touches any one of the displayed images 234A to 234H. When the reception of the size setting is not changed, the next processing executes while the current region of interest is maintained. A numeral written on the upper right side of each illustration indicates the diameter (mm) of the region of interest, and a numeral written on the lower right side of each illustration indicates the height (mm) of the region of interest. The upper and lower jaws can be imaged in the case that the height of the region of interest is 80, and only one of the upper and lower jaws can be imaged to reduce the radiation dose in the case that the height of the region of interest is 40 or 50.

The imaging area setting image 234 may be changed depending on the setting of the region-of-interest setting image 231. For example, in the case that the maxillofacial area is set to the region of interest, the imaging area setting image 234 is set to an image in which the size of the entire maxillofacial area as a target, for example, the range of the diameter of 150 mm as the imaging area.

The scan mode selection image 235 is an image used to set the turning angle of the turning support 124 necessary for the X-ray CT imaging, and is an image used to set a mode whether the X-ray CT imaging is performed by 180° turning or 360° turning.

In the operation panel device 158, a radiation setting image 241, a tube voltage setting image 242, a tube current setting image 243, and a sensitivity setting image 244 are displayed as an imaging condition setting image. In this case, these images are displayed in the lower portion of the operation panel device 158.

The radiation setting image 241 is an image in which a character "M" representing the manual setting is added below a character "Exp". The manual setting of the tube voltage, the tube current, and the resolution and the turning-off of the X ray (set when the arm is rotated without radiation) can be set using the setting of the radiation setting image 241. What is currently selected may be displayed depending on the content displayed below the character "Exp". As illustrated in the drawings, the current selection is the manual setting when the character "M" is displayed. Other options may be displayed by touching the place of the character "M". For example, the manual setting, automatic setting, and the turning-off of the X-ray may be selected such that the character "M", the character "A" and the character "Off" are displayed by this selection. As the automatic setting, it is conceivable to set a pattern that gives the intensity to the dose of the X-ray during the X-ray imaging, and another character may be displayed in the case that the pattern with the intensity is selected.

Further, in the case that the manual setting is selected, the low dose mode is released, and the same radiation condition may be applied regardless of imaging information such as the imaging area. For example, in selecting the manual setting is selected for a certain imaging area, in the case that the operation is performed such that the tube current becomes 8 mA, the same tube current 8 mA may be applied even if another imaging area is set. Hereinafter, a mode in which the same radiation condition is applied is referred to as a multi-condition mode. The low dose mode and the multi-condition mode may be selectable. At least one of the low dose mode, the high resolution mode, and the multi condition mode may be selected. These selections may be made by operating the radiation mode setting image 220.

Figure 12:
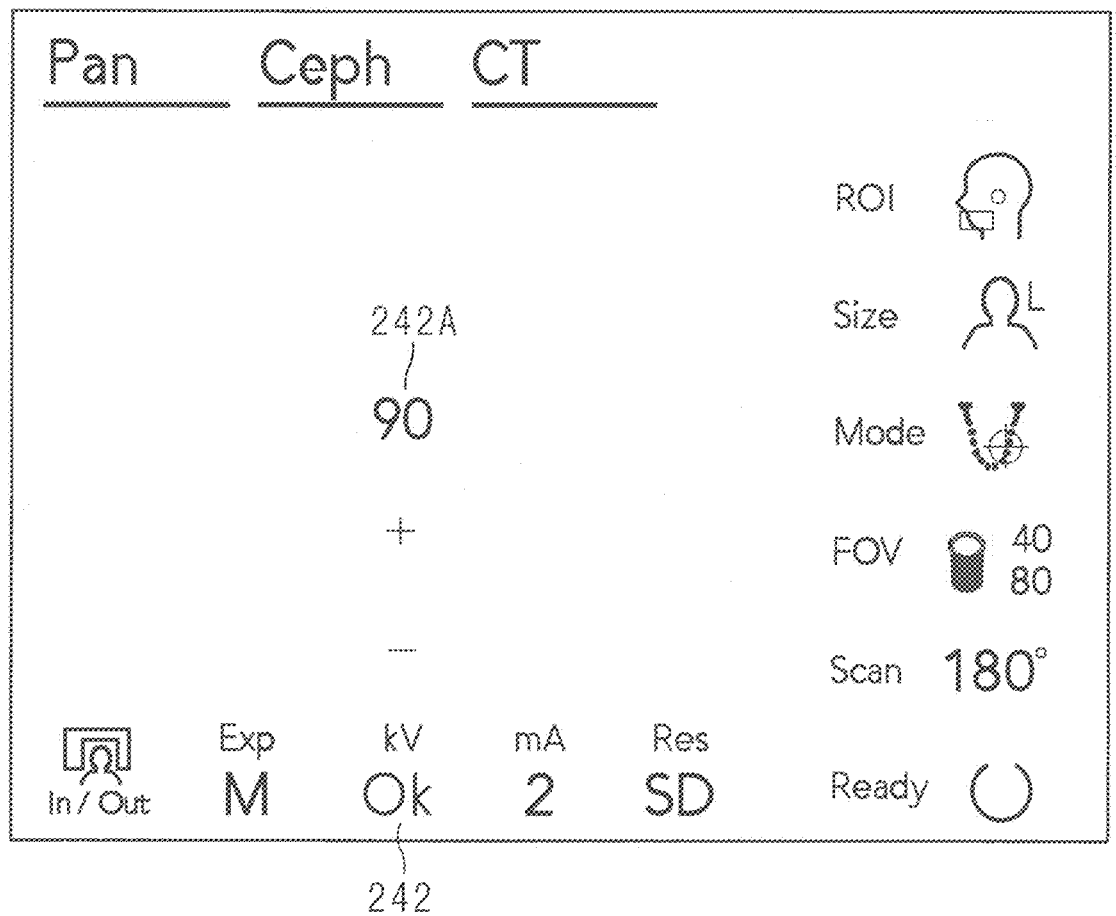
FIG. 12 is a view illustrating a setting display example of the operation panel device.

The tube voltage setting image 242 is an image in which a numeral representing the tube voltage setting value is added under a character "kV" representing a tube voltage unit. When the user touches the tube voltage setting image 242, a tube voltage adjustment image 242A is displayed as illustrated in FIG. 12. The tube voltage adjustment image 242A includes a symbol "+" increasing the tube voltage, a symbol "−" decreasing the tube voltage, and a numerical value display place indicating the tube voltage. Then, the setting value of the tube voltage is increased when the user touches the symbol "+", and the setting value of the tube voltage is decreased when the user touches the symbol "−", and each setting value is displayed as a numeral value. The character "OK" is displayed in the state in which the tube voltage adjustment image 242A is displayed. When the operator touches the character "OK" is touched after the tube voltage setting is ended, the tube voltage adjustment image 242A disappears, and the tube voltage setting image 242 is displayed while the setting value is reflected.

Figure 13:
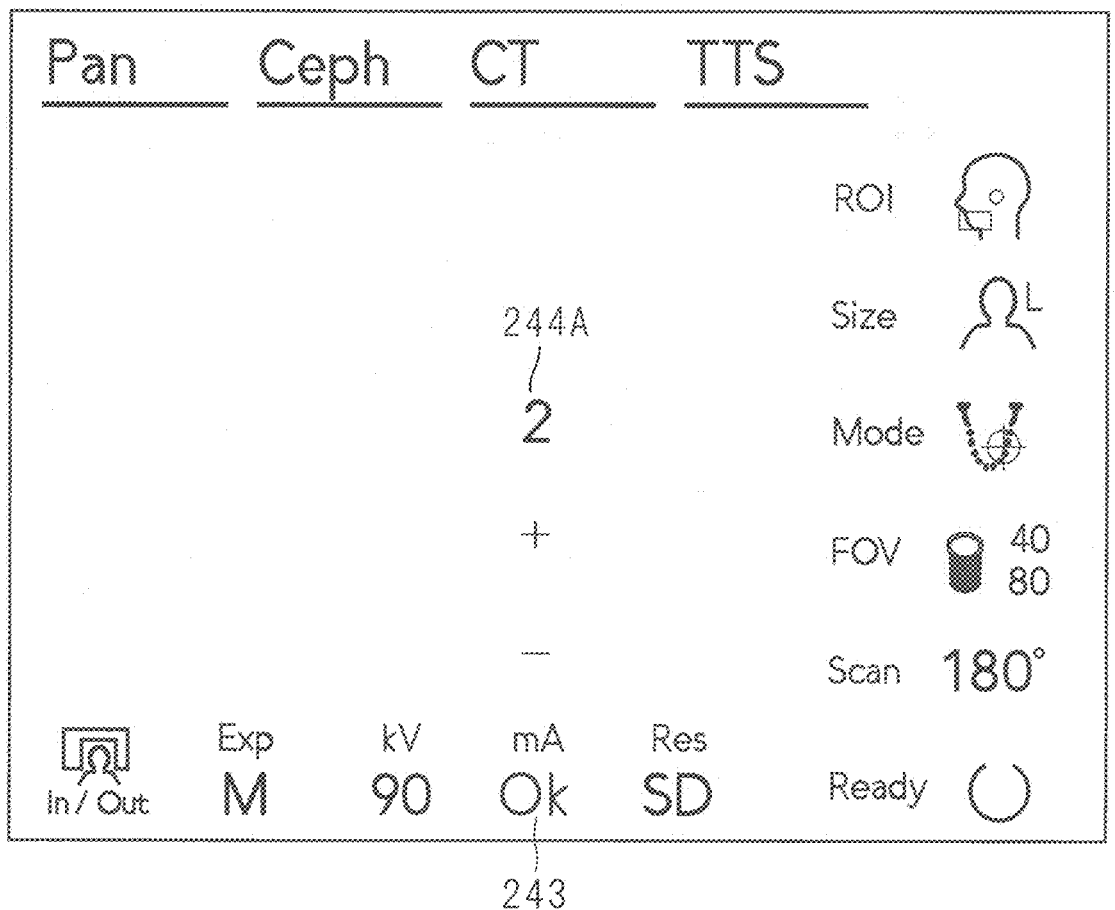
FIG. 13 is a view illustrating a setting display example of the operation panel device.

The tube current setting image 243 is an image in which a numeral representing the tube current setting value is added below a character "mA" representing a tube current unit. When the user touches the tube current setting image 243, a tube current adjustment image 243A is displayed as illustrated in FIG. 13. The tube current adjustment image 243A includes a symbol "+" increasing the tube current, a symbol "−" decreasing the tube current, and a numerical value display place for indicating the tube current. The setting value of the tube current is increased when the user touches the symbol "+", and the setting value of the tube current is decreased when the user touches the symbol "−", and each setting value is displayed as a numeral value. The character "OK" is displayed in the state in which the tube current adjustment image 243A is displayed. When the operator touches the character "OK" is touched after the tube current setting is ended, the tube current adjustment image 243A disappears, and the tube current setting image 243 is displayed while the setting value is reflected.

The sensitivity setting image 244 is an image used to manually set the sensitivity per unit area of the detection surface of the X-ray detector 128. For example, a standard and high sensitivity can be selected as the sensitivity, a character "SD" may be displayed for the standard, and a character "HR" may be displayed for the high resolution.

The display position of each of the image is not limited to the example in FIG. 7, but can be set to any position.

<Example of Reference Table>

An example of the reference table will be described with reference to FIG. 14.

In the reference table, the low dose mode and the high resolution mode are separately set. In each mode, the child and the adult (the physique exceeding the child) are separately set.

As to the size of the adult in the low dose mode, in the case that the imaging area has the diameter of 40 mm, the output condition of the X-ray generator 126 is set to the tube voltage of 100 kV and the tube current of 8 mA. The voxel size is set to 80 μm as the setting relating to the image quality. The size of the imaging area may be set as the size of the imaging area in a plane orthogonal to the turning axis of the turning drive unit 30 (that is, a plane parallel to the floor). The diameter is defined for a circular shape in the case that the imaging area on the plane has the circular shape, and the diameter of a circumscribed circle is defined for the imaging area when the imaging area on the plane has a noncircular shape.

On the other hand, in the case that the imaging area has the diameter of 80 mm or 100 mm, the case that the imaging area has the diameter of 80 mm or 100 mm differs from the above output condition in that the tube current is set to 7 mA. The case that the imaging area has the diameter of 80 mm or 100 mm also differs from the above output condition in that the voxel size is set to 125 μm as the setting relating to the image quality.

For this reason, in the case that the imaging area has the diameter of 80 mm or 100 mm, the output condition is set such that the dose becomes smaller as compared with the case that the imaging area has the diameter of 40 mm. In the case that the imaging area has the diameter of 80 mm or 100 mm, the voxel size is set larger than the case that the imaging area has the diameter of 40 mm. As a result, although the resolution becomes coarse, the setting is performed such that the image quality in which the noise is reduced is obtained.

The case that the imaging area has the diameter of 150 mm differs from the case that the imaging area has the diameter of 40 mm, 80 mm or 100 mm in that the tube current is set to 6 mA. The case that the imaging area has the diameter of 150 mm also differs from the case that the imaging area has the diameter of 40 mm, 80 mm or 100 mm in that the voxel size is set to 320 μm as the setting relating to the image quality.

In the case that the imaging area has the diameter of 150 mm, the output condition is set such that the dose becomes smaller than that of each of the above examples. In the case that the imaging area has the diameter of 150 mm, the voxel size is set larger than that of each of the above examples. As a result, although the resolution becomes coarse, the setting is performed such that the image quality in which the noise is reduced is obtained.

Assuming that the imaging area having the diameter of 40 mm is a first imaging area, and assuming that the imaging area having the diameter of 80 mm or 100 mm is a second imaging area, the first output condition (the tube voltage of 100 kV, the tube current of 8 mA) and the second output condition (the tube voltage of 100 kV, the tube current of 7 mA) are specified such that the dose based on the first output condition corresponding to the size of the first imaging area is larger than the dose based on the second output condition corresponding to the size of the second imaging area (relatively, the dose based on the second output condition corresponding is smaller than the dose based on the first output condition). Based on the reference table 152, the X-ray output condition setting unit 152d automatically sets the first output condition and the second output condition such that the above condition is satisfied.

Assuming that the imaging area having the diameter of 80 mm or 100 mm is a first imaging area, and assuming that the imaging area having the diameter of 150 mm is a second imaging area, the first output condition (the tube voltage of 100 kV, the tube current of 7 mA) and the second output condition (the tube voltage of 100 kV, the tube current of 6 mA) are specified such that the dose based on the first output condition corresponding to the size of the first imaging area is larger than the dose based on the second output condition corresponding to the size of the second imaging area (relatively, the dose based on the second output condition corresponding is smaller than the dose based on the first output condition). Based on the reference table 152, the X-ray output condition setting unit 152d automatically sets the first output condition and the second output condition such that the above condition is satisfied.

It can also be understood that the imaging area having the diameter of 150 mm is the setting in which the maxillofacial area of the subject P is set to the imaging area, that the imaging area having the diameter of 40 mm is the first imaging area in which a part of the teeth of the dental arch is contained, and that the imaging area having the diameter of 80 mm or 100 mm is an example of the area in which the whole area of the dental arch or all the teeth of the dental arch is contained.

However, the size of each imaging area needs not to be the above example.

For example, it is considered that the case that a part of the dental arch is set to the imaging area and the case that the entire dental arch is set to the imaging area as much as possible are distinguished from each other by the size of the imaging area. In this case, when the imaging information receiving unit 152c can receive the setting of the imaging area where a boundary circle or a circumscribed circle has a diameter of R1 (mm) as the first imaging area while receiving the setting of the imaging area where a boundary circle or a circumscribed circle has a diameter of R2 (mm) as the second imaging area, a condition of R1 (mm)<k1 (mm)<R2 (mm) may be satisfied for a value k1 satisfying 40 (mm)<k1 (mm)<70 (mm).

For example, it is considered that the case that the entire dental arch is set to the imaging area as much as possible and the case that the entire jaw is set to the imaging area as much as possible are distinguished from each other by the size of the imaging area. In this case, when the imaging information receiving unit 152c can receive the setting of the imaging area where a boundary circle or a circumscribed circle has a diameter of R1 (mm) as the first imaging area while receiving the setting of the imaging area where a boundary circle or a circumscribed circle has a diameter of R2 (mm) as the second imaging area, a condition of R1 (mm)<k2 (mm)<R2 (mm) may be satisfied for a value k2 satisfying 80 (mm)<k2 (mm)<120 (mm).

As to the physique of the child in the low dose mode, the tube voltage is set to 90 kV smaller than that of the above examples. For this reason, in the reference table 152, at least one setting value defining each of the output condition corresponding to the physique exceeding the child and the output condition corresponding to the physique of the child are defined such that the dose based on the output condition corresponding to the physique exceeding the child is larger than the dose based on the output condition corresponding to the physique of the child. Thus, based on the reference table 152, the X-ray output condition setting unit 152d automatically sets at least one setting value defining each of the output condition corresponding to the physique exceeding the child and the output condition corresponding to the physique of the child such that the dose based on the output condition corresponding to the physique exceeding the child is larger than the dose based on the output condition corresponding to the physique of the child.

The dose during X-ray CT imaging can be adjusted by the tube voltage, the tube current, a radiation time of the X-ray generator 126, and the like. For example, the dose is decreased when the radiation time of the X-ray detector 128 is shortened, and the dose is increased when the irradiation time is lengthened. For example, the radiation time can be adjusted by controlling the speed at which the X-ray generator 126 is rotated. The dose can be switched by adjusting the angle at which the X-ray generator 126 is turned (for example, switching between 180° turning or 360° turning).

The dose during the X-ray CT imaging can be set theoretically, experimentally and empirically by adjusting the tube voltage, tube current, and the radiation time of the X-ray generator 126 in combination.

In the high resolution mode, the tube current is uniformly set to 8 mA as compared with the low dose mode. Additionally, the voxel size is uniformly set as 80 μm as the setting relating to the image quality. Consequently, in the high resolution mode, the sharp X-ray CT image can be obtained with the relatively high dose. The tube current is uniformly set to 9 mA, and a difference may be made between the low dose mode and the high resolution mode even for the imaging area having the diameter of 40 mm. The operation of the operator to access and rewrite the numerical value of the reference table can be received.

For example, in the low resolution mode, with respect to an imaging area with a diameter of 40 mm for an adult's physique the output condition in the case of the maxillary molar area is set to a tube voltage of 100 kV, a tube current of 7.5 mA, with respect to an imaging area with a diameter of 40 mm for a child's physique, the output condition in the case of the maxillary molar area is set to a tube voltage of 90 kV, a tube current of 7.5 mA, it may be attenuated more than that in the same region in the high resolution mode. It may be expanded by setting the image quality setting voxel size to 90 μm, for example, by weakening amount of the tube current.

Further, output condition setting for each imaging region may be added. For example, in the low resolution mode, with respect to the imaging area having a diameter of 40 mm, the output condition in the case of the maxillary molar area is set to a tube voltage of 100 kV, a tube current of 8 mA, and the output condition of the mandibular anterior tooth area is set to a tube voltage of 100 kV, a tube current of 5 mA, it may be varied for each part.

<Action>

Figure 15:
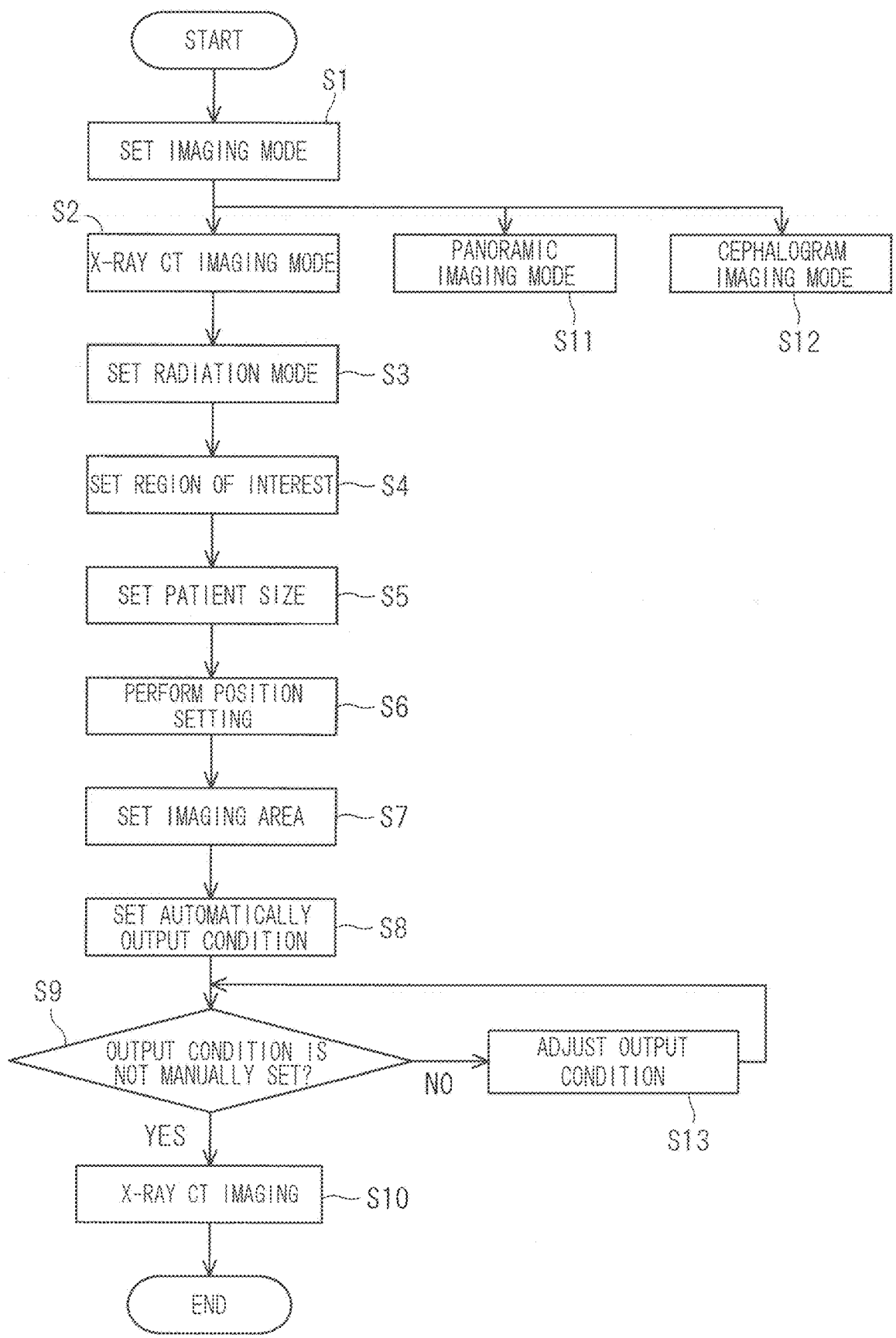
FIG. 15 is a flowchart illustrating a processing example of the X-ray CT imaging apparatus.

Action of the X-ray CT imaging apparatus 110 will be described with reference to FIG. 15 by focusing on X-ray CT imaging action.

In step S1, when the user touches one of the imaging mode selection images 201, 202, 203, one of the panoramic imaging mode, the cephalogram imaging mode, or the CT imaging mode is selectively received (see FIG. 7). When the setting of the panorama imaging mode is received, the flowchart goes to step S11 to perform the panorama imaging processing. When setting of the cephalometric imaging mode is received, the flowchart goes to step S12 to perform the cephalogram imaging processing. When the setting of the CT imaging mode is received, the flowchart goes to pieces of processing from step S2.

In step S2, it is determined that the mode is a mode in which CT imaging is performed.

In step S3, the setting of the radiation mode is received using the radiation mode setting image 220 (see FIGS. 7 and 8).

In step S4, the setting of the region of interest is received through the region-of-interest setting image 231 (see FIG. 9).

In step S5, the setting of the patient size (physique) is received through the patient size setting image 232 (see FIG. 10). As described above, the setting of the patient size (physique) includes setting whether the physique is the child or the physique exceeding the child.

In step S6, the position setting is received through the imaging area setting image 234 and the imaging position designating image 210 (see FIG. 7). Consequently, the setting of the imaging position is received.

In step S7, the size of the imaging area is set through the imaging area setting image 234 (see FIG. 11).

In step S8, the output condition of the X-ray generator 126 is automatically set. At this point, the reference table 152 in FIG. 14 is referred to, and the output condition of the X-ray generator 126 is automatically set based on the size of the imaging area and whether the physique is the size of the child or the size exceeding the child (that is, the adult).

After the automatic setting, the flowchart goes to step S9 to determine whether the output condition is manually set. When the user manually sets the tube voltage and the tube current through the tube voltage setting image 242 and the tube current setting image 243, the flowchart goes to step S13 to set the output condition based on the manual setting, and the flowchart returns to step S9. The determination in step 9 after step 8 is the determination as to presence or absence of an operation for manual setting, and the determination in step 9 after step 13 is the determination as to the presence or absence of a newly added manual setting operation.

When it is determined in step S9 that the output condition is not manually set, the flowchart goes to step S10.

In step S10, the X-ray CT imaging is performed according to the set output condition. The X-ray CT image is generated based on the data obtained by the X-ray CT imaging. In generating the X-ray CT image, the X-ray CT image is generated according to the setting relating to the above image quality (in this case, the setting of the voxel size). The above steps can be changed as appropriate. For example, the order of step 6 and step 7 may be exchanged.

<Effect>

According to the medical X-ray CT imaging apparatus 110, the medical X-ray CT imaging condition setting method, and the X-ray CT imaging condition setting program 151a configured as described above, the medical X-ray CT imaging apparatus 110 includes the X-ray generator 126, the X-ray detector 128, the turning support 124, and the motor 132a as the turning drive unit, and the X-ray CT imaging apparatus 110 receives the setting of the imaging area relating to at least one of the size of the imaging area, the imaging purpose, and the imaging region is accepted, and automatically sets the output condition of the X-ray generator 126 according to at least received one of the size of the imaging area, the imaging purpose, and the imaging region, which allows achievement of the radiation exposure as low as possible. When the size of the imaging area or the imaging region is typically set according to the imaging purpose, the X-ray CT image having the adequate image quality can be obtained according to the imaging purpose by automatically setting the output condition of the X-ray generator 126 according to at least one of the size of the imaging area, the imaging purpose, and the imaging region.

The noise is easily included in the X-ray CT image under the X-ray output condition aimed at the low dose. By automatically setting the image quality of the X-ray CT image according to at least one of the setting of the imaging area and the automatically-set output condition of the X-ray generator 126, the noise can be reduced in the case that the X-ray CT imaging is performed under the X-ray output condition aimed at the low dose.

In particular, by setting the size in the plane orthogonal to the turning axis to the received size of the imaging area, the output condition of the X-ray generator can automatically be set according to the spread of the imaging area on that plane.

The relatively small imaging area is set in the case that details are observed in detail, and the relatively large imaging area is set in the case that the whole observation is performed. The settings of the first imaging area and the second imaging area wider than the first imaging area are received as the setting relating to the size of the imaging area, and at least one setting value defining the first output condition and the second output condition is automatically set such that the dose based on the second output condition corresponding to the size of the second imaging area is smaller than the dose based on the first output condition corresponding to the size of the first imaging area, which allows the X-ray CT imaging to be performed under the output condition suitable for the imaging purpose.

In consideration of the first imaging area and the second imaging area, in the case that the area in which a part of the teeth of the dental arch is contained is set as the first imaging area, the X-ray CT imaging can be performed under the first output condition that the dose becomes relatively large, and a part of the teeth of the dental arch can be observed with the relatively sharp image. On the other hand, in the case that the area in which the entire area of the dental arch or all the teeth of the dental arch is contained is set as the second imaging area, the X-ray CT imaging of the dental arch can be performed under the second output condition that the dose becomes relatively small.

In addition to the received imaging area, the radiation exposure can be achieved as low as possible by automatically setting the output condition of the X-ray detector 128 according to the setting of the physique.

Specifically, when the physique is set to the child, the dose can be decreased and the exposure dose can be decreased. On the other hand, when the subject is set to the physique exceeding the child, the sharp image can be obtained by increasing the dose.

The dose can be adjusted by automatically setting at least one of the tube voltage and the tube current of the X-ray generator 126 and the time during which the X-ray generator 126 emits the X-ray as the output condition of the X-ray detector 128.

The low dose mode and the high resolution mode can be switched, and the output condition of the X-ray generator is automatically set according to the information about the received imaging area when the low dose mode is received, which allows the X-ray CT image having the appropriate image quality to be obtained according to the purpose of imaging while the exposure dose is achieved as low as possible. When the high resolution mode is received, the sharp X-ray CT image can be obtained regardless of the information about the received imaging area. After the output condition of the X-ray generator 126 is automatically set according to the information about the received imaging area, the output condition of the X-ray generator 126 can be changed by the manual setting according to operator's preference.

A control example of the output condition of the X-ray generator 126 will be described below from the viewpoint of a radiation X-ray amount.

As described above, the detection surface of the X-ray detector 128 is constructed with the pixels. When each pixel has a rectangular shape, the shape of the X-ray beam emitted from a focal point of the X-ray tube to each pixel has a substantially quadrangular pyramid shape. For example, the radiation X-ray amount contained in the space formed by the substantially quadrangular pyramid-shaped X-ray beam for each pixel is increased when the tube current is increased, and the radiation X-ray amount is decreased when the tube current is decreased. Similarly, for example, the radiation X-ray amount contained in the space formed by the substantially quadrangular pyramid-shaped X-ray beam for each pixel is increased when the tube voltage is increased, and the radiation X-ray amount is decreased when the tube voltage is decreased. Similarly, for example, the radiation X-ray amount contained in the space formed by the substantially quadrangular pyramid-shaped X-ray beam for each pixel in performing evaluation over the entire irradiation time is increased when the irradiation time of the X-ray is lengthened, and the radiation X-ray amount in performing the evaluation over the entire irradiation time is decreased when the radiation time of the X-ray is shortened.

When this is considered on the side of the X-ray detector 128, in the case that an attenuating element such as the subject does not exist between the X-ray generator 126 and the X-ray detector 128, a light receiving amount of each pixel is increased when the tube current is increased, and the light receiving amount is decreases when the tube current is decreased. Similarly, the light receiving amount is increased when the tube voltage is increased, and the light receiving amount is decreased when the tube voltage is decreased. Similarly, the light receiving amount of each pixel is increased when the radiation time of the X-ray is lengthened, and the light receiving amount is decreased when the radiation time of the X-ray is shortened. Unless the irradiation conditions including the tube current, the tube voltage, and the irradiation time are changed by a plurality of times of the X-ray irradiation, the light receiving amount of each pixel becomes identical.

In this way, it is conceivable that the output condition is changed such that the radiation X-ray amount is increased or decreased with respect to the unit area of the detection surface of the X-ray detector 128 (this is also the increase and decrease of the X-ray amount passing through the unit space such as the substantially quadrangular pyramid-shaped space). Assuming that the attenuating element such as the subject does not exist between the X-ray generator 126 and the X-ray detector 128, the increase or decrease of the radiation X-ray amount with respect to the unit area of the detection surface of the X-ray detector 128 is equivalent to the increase or decrease of the light receiving amount per unit area of the detection surface of the X-ray detector 128.

For example, an area of each pixel unit and an area of each binning unit in the case that the plurality of pixels are binned can be considered as the unit area.

Thus, an example in which the X-ray radiation output to a certain imaging area AR1 is smaller than the X-ray irradiation output to another imaging area AR2 can be adopted as an example in which the output condition of the X-ray generator is automatically set according to at least one of the size of the imaging area, the imaging purpose, and the imaging region, which are received by the imaging information receiving unit. For example, the tube current can be decreased lower than the imaging area AR2 relative to the imaging area AR1, and the radiation X-ray amount per unit area can be decreased smaller than the imaging area AR2 relative to the imaging area AR1 (assuming that the attenuating element such as the subject is retracted from between the X-ray generator 126 and the X-ray detector 128, the imaging area AR2 can be larger than the imaging area AR1 in the light receiving amount per unit area). Similarly, for example, the tube voltage can be decreased lower than the imaging area AR2 relative to the imaging area AR1, and the imaging area AR2 can be smaller than the imaging area AR1 in the radiation X-ray amount per unit area. Similarly, for example, the irradiation time can be shorter than the imaging area AR2 relative to the imaging area AR1, and the imaging area AR2 can be smaller than the imaging area AR1 in the radiation X-ray amount per unit area. The imaging area AR2 can be smaller than the imaging area AR1 in the radiation X-ray amount per unit area by adjusting the combination of the tube current, the tube voltage, and the radiation time.

The term that the X-ray radiation output to the imaging region AR1 is equalized to the X-ray radiation output to the imaging region AR2 means that the radiation X-ray amount per unit area is equalized (assuming that the attenuating element such as the subject is retracted from between the X-ray generator 126 and the X-ray detector 128, the light receiving amount per unit area is equalized unless the radiation condition including the tube current is changed.

(Modifications)

Figures 16, 17:
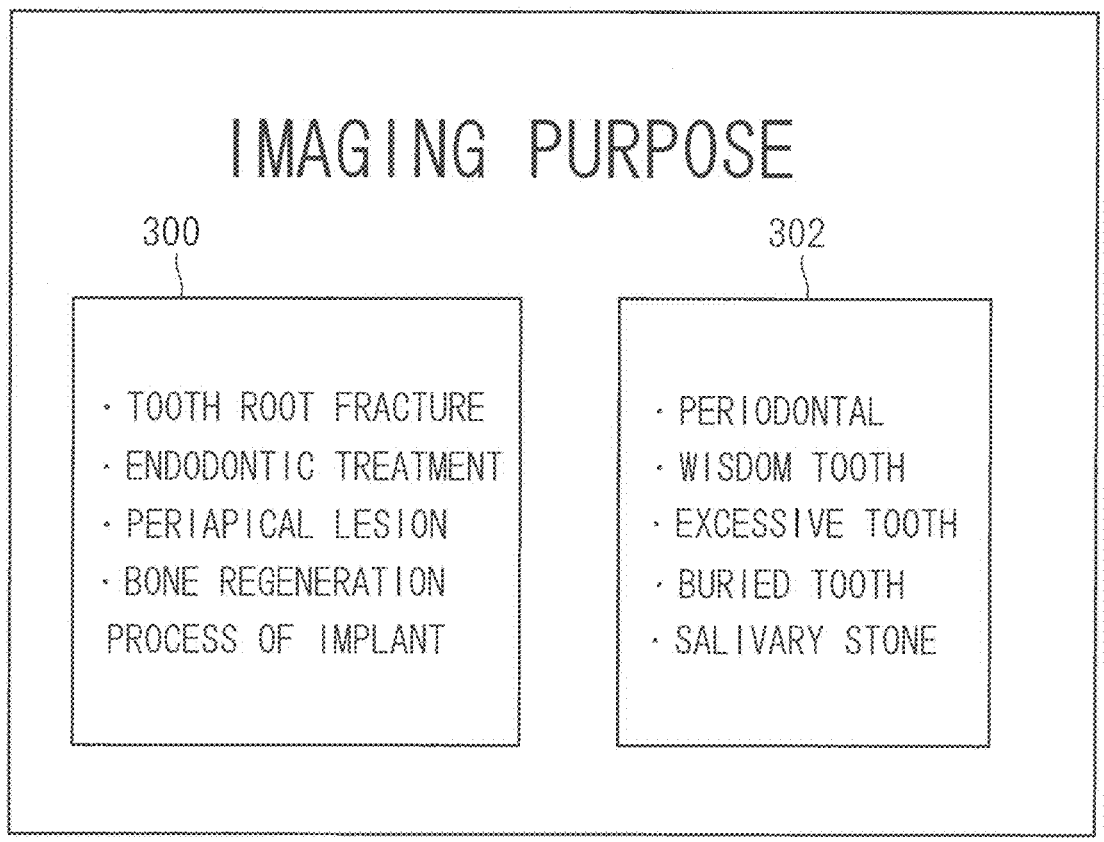
FIG. 16 is a view illustrating another example of the reference table.
FIG. 17 is a view illustrating a setting display example of the operation panel device.

An example of a reference table in the case that the radiation time is changed among setting values defining output condition of the X-ray generator 126 is illustrated an a modification in FIG. 16.

As illustrated in FIG. 16, the same for the size of the imaging range having the diameter of 40 mm is identical to the imaging range having the diameter of 80 mm or 100 mm in the tube voltage of 100 kV and the tube current of 8 mA. However, the radiation time of the former is set to 17.9 s, and the irradiation time of the latter is set to 9.4 s, whereby the former is larger than the latter in the dose during the X-ray CT imaging. It is assumed that the turning angle of the X-ray detector 128 (or the turning support 124) is the same range AG1, and the time necessary for the turning of the angle AG1 is switched between the radiation time 17.9 s and the radiation time 9.4 s. The radiation time may be changed by switching the turning angle of the X-ray detector 128 (or the turning support 124). For example, the turning angle is switched between 360° and 180°. In this case, the setting of the radiation time to 17.9 s means that the X-ray detector 128 has the turning angle of 360°, and the setting of the radiation time to 9.4 s means that the X-ray detector 128 has the turning angle of 180°. With respect to the size of the imaging area having a diameter of 150 mm, by setting the irradiation time to 9.4 s and the tube current to 6 mA, and by decreasing the tube current, whereby the dose at the time of X-ray CT imaging is set to be reduced rather than with respect to the size of the imaging area of 80 mm or 100 mm in diameter.

In the above preferred embodiments, by way of example, the output condition of the X-ray detector 128 is set according to the size of the imaging range. Alternatively, the imaging information receiving unit may receive the setting of the imaging area relating to at least one of the size of the imaging area, the imaging purpose, and the imaging region, and the output condition of the X-ray generator may automatically be set according to at least one of the size, the imaging purpose, and the imaging region, which are received by the imaging information receiving unit.

For example, as illustrated in FIG. 17, a setting screen for the imaging purpose is provided on the operation panel device 158, a purpose selection image 300 that allows the user to select the tooth root fracture, the endodontic treatment, the periapical lesion, and the bone regeneration process of the implant as the observation purpose and a purpose selection image 302 that allows the user to select to use as the object of observation the purpose selection image 300 that allows the user to select the periodontal, the wisdom tooth, the excessive tooth, the buried tooth, and the salivary stone as the observation purpose are displayed in the setting screen for the imaging purpose, and the user touches one of the purpose selection images 300, 302, which allows the main body controller 150 to receive the setting for the imaging purpose.

In the case that the imaging purposes of the tooth root fracture, the endodontic treatment, the periapical lesion, and the bone regeneration process of the implant are set as the reference table as illustrated in FIG. 18, the sharp X-ray CT image is preferably obtained, so that the output condition is set such that the dose becomes relatively large. At this point, the tube voltage is set to 100 kV and the tube current is set to 8 mA.

In the case that the imaging purposes of the periodontal, the wisdom tooth, the excessive tooth, the buried tooth, and the salivary stone are set, the rough observation is performed, so that the output condition that the dose becomes relatively small may be set such that the exposure dose can be decreased as low as possible. At this point, the tube voltage is set to 100 kV and the tube current is set to 6 mA.

Consequently, the output condition of the X-ray generator 126 can be automatically set according to the set imaging purpose.

For example, as in a reference table of FIG. 19, the output condition of the X-ray detector 128 may be automatically set according to the imaging region in the imaging range specified in the imaging position designating image 210. The designation of the imaging region may be performed by the designation of the X-ray image subjected to the designation of the dental arch or the cephalogram imaging. Discrimination of the imaging region can be performed by discriminating the range of teeth included in the designated imaging range.

In the case that the imaging regions of the lower anterior tooth, the mandibular molar, the upper anterior tooth, and the maxillary molar are set, the skull base having a large X-ray absorption coefficient does not enter the path of the X-ray cone beam, so that the output condition that the dose is relatively small is set such that the exposure dose can be decreased as low as possible. At this point, the tube voltage is set to 100 kV and the tube current is set to 6 mA.

In the case that the imaging region of the temporomandibular joint is set, the output condition that the dose relatively large is set because the skull base enters the path of the X-ray cone beam. The tube voltage is set to 100 kV and the tube current is set to 8 mA.

Consequently, the output condition of the X-ray generator 126 can automatically be set according to the set imaging region.

The output condition of the X-ray generator 126 may automatically be set according to a plurality of combinations of the size of the imaging area, the imaging purpose, and the imaging region. In this case, for example, as illustrated in FIG. 20, the imaging purpose and the imaging region are specified with respect to the size of the imaging area as necessary, and the reference table in which the output condition of the X-ray generator 126 and the and image quality are set for each combination may be prepared. FIG. 21 illustrates an example in which the output condition of the X-ray generator 126 and the image quality are set for the combination of the imaging purpose and the imaging region with respect to the imaging area having the diameter of 40 mm. Alternatively, the output condition of the X-ray generator 126 and the image quality may be set for the combination of the imaging purpose and the imaging region with respect to the imaging areas having other sizes.

The respective configurations described in the above preferred embodiments and modifications can appropriately be combined as long as they are inconsistent each other. For example, each unit of the second preferred embodiment can be combined with the configuration of the first preferred embodiment.

Although the present invention is described above in detail, the above description is illustrative in all aspects, but the invention is not limited thereto. Innumerable modifications not illustrated can be envisaged without departing from the scope of the present invention.

While the invention has been shown and described in detail, the foregoing description is in all aspects illustrative and not restrictive. It is therefore understood that numerous modifications and variations can be devised without departing from the scope of the invention.

What is claimed is:

1. A medical X-ray CT imaging apparatus comprising:
an X-ray generator that generates a cone beam;
an X-ray detector;
a support that supports said X-ray generator and said X-ray detector while said X-ray generator and said X-ray detector are opposed to each other;
an actuator that turns said X-ray generator and said X-ray detector, which are supported by said support; and
a processor,
wherein, when a setting of an imaging area relating to at least one of a size of the imaging area, an imaging purpose, and an imaging region is input as imaging information, the processor sets automatically an output condition of said X-ray generator according to at least one of the size of the imaging area, the imaging purpose, and the imaging region, which are input,
said processor is configured to receive settings of a first imaging area and a second imaging area wider than said first imaging area as said setting relating to said size of said imaging area, and automatically sets at least one setting value defining a first output condition for a dose based on said first output condition corresponding to said size of said first imaging area, and a second output condition for a dose based on said second output condition corresponding to said size of said second imaging area,
said processor is further configured to receive a setting of an imaging area where a boundary circle or a circumscribed circle has a diameter of R1 (mm) as said first imaging area while receiving a setting of an imaging area where a boundary circle or a circumscribed circle has a diameter of R2 (mm) as said second imaging area, where, for a value k1 satisfying 40 (mm)<k1 (mm)<70 (mm), an expression of R1 (mm)<k1 (mm)<R2 (mm) is satisfied.

2. The medical X-ray CT imaging apparatus according to claim 1, wherein said dose based on said second output condition corresponding to said size of said second imaging area is smaller than said dose based on said first output condition corresponding to said size of said first imaging area.

3. The medical X-ray CT imaging apparatus according to claim 1, wherein said processor automatically sets image quality of an X-ray CT image according to at least one of said setting of said imaging area received by said processor and said output condition of said X-ray generator set by said processor.

4. The medical X-ray CT imaging apparatus according to claim 1, wherein said processor receives said setting of said size of said imaging area on a plane orthogonal to a turning axis of said actuator as said setting relating to said size of said imaging area.

5. The medical X-ray CT imaging apparatus according to claim 1, wherein said processor is further configured to receive a setting of an area, where a maxillofacial area of a subject is set to said imaging area and a tooth of a part of a dental arch is contained, to said first imaging area and a setting of an area, where the maxillofacial area of the subject is set to said imaging area and an entire area of the dental arch or all the teeth of the dental arch are contained, to said second imaging area, as said setting relating to said size of said imaging area.

6. The medical X-ray CT imaging apparatus according to claim 1, wherein
said processor is further configured to receive a setting of a physique, and
said processor automatically sets said output condition of said X-ray generator according to said setting of said physique in addition to said setting of said imaging area relating to at least one of said size of said imaging area, said imaging purpose, and said imaging region, which are received by said processor.

7. The medical X-ray CT imaging apparatus according to claim 6, wherein
said processor receives a setting whether a subject is a physique of a child or a physique exceeding the physique of the child as said setting of said physique, and
said processor automatically sets at least one setting value defining an output condition corresponding to the physique exceeding the physique of the child and an output condition corresponding to the physique of the child such that a dose based on the output condition corresponding to the physique exceeding the physique of the child is larger than a dose based on the output condition corresponding to the physique of the child.

8. The medical X-ray CT imaging apparatus according to claim 1, wherein said processor automatically sets at least one of a tube voltage of said X-ray generator, a tube current of said X-ray generator, and time during which said X-ray generator emits an X-ray as said output condition of said X-ray generator.

9. The medical X-ray CT imaging apparatus according to claim 1, wherein said processor receives settings of a low dose mode and a high resolution mode,
wherein said processor automatically sets said output condition of said X-ray generator according to said setting of said imaging area when said low dose mode is received by said processor.

10. A medical X-ray CT imaging apparatus comprising:
an X-ray generator that generates a cone beam;
an X-ray detector;
a support that supports said X-ray generator and said X-ray detector while said X-ray generator and said X-ray detector are opposed to each other;
an actuator that turns said X-ray generator and said X-ray detector, which are supported by said support; and
a processor,
wherein, when a setting of an imaging area relating to at least one of a size of the imaging area, an imaging purpose, and an imaging region is input as imaging information, the processor sets automatically an output condition of said X-ray generator according to at least one of the size of the imaging area, the imaging purpose, and the imaging region, which are input,
said processor is configured to receive settings of a first imaging area and a second imaging area wider than said first imaging area as said setting relating to said size of said imaging area, and automatically sets at least one setting value defining a first output condition for a dose based on said first output condition corresponding to said size of said first imaging area, and a second output condition for a dose based on said second output condition corresponding to said size of said second imaging area, said processor is further configured to receive a setting of an imaging area where a boundary circle or a circumscribed circle has a diameter of R1 (mm) as said first imaging area while receiving a setting of an imaging area where a boundary circle or a circumscribed circle has a diameter of R2 (mm) as said second imaging area, where, for a value k2 satisfying 80 (mm)<k2 (mm) <120 (mm), an expression of R1 (mm)<k2 (mm)<R2 (mm) is satisfied.

11. The medical X-ray CT imaging apparatus according to claim 10, wherein said dose based on said second output condition corresponding to said size of said second imaging area is smaller than said dose based on said first output condition corresponding to said size of said first imaging area.

12. The medical X-ray CT imaging apparatus according to claim 10, wherein the processor automatically sets image quality of an X-ray CT image according to at least one of said setting of said imaging area received by said processor and said output condition of said X-ray generator set by said processor.

13. The medical X-ray CT imaging apparatus according to claim 10, wherein said imaging information receiving unit receives said setting of said size of said imaging area on a plane orthogonal to a turning axis of said actuator as said setting relating to said size of said imaging area.

14. The medical X-ray CT imaging apparatus according to claim 10, wherein said processor is further configured to receive a setting of an area, where a maxillofacial area of a subject is set to said imaging area and a tooth of a part of a dental arch is contained, to said first imaging area and a setting of an area, where the maxillofacial area of the subject is set to said imaging area and an entire area of the dental arch or all the teeth of the dental arch are contained, to said second imaging area, as said setting relating to said size of said imaging area.

15. The medical X-ray CT imaging apparatus according to claim 10, wherein
said processor is further configured to receive a setting of a physique, and
said processor automatically sets said output condition of said X-ray generator according to said setting of said physique in addition to said setting of said imaging area relating to at least one of said size of said imaging area, said imaging purpose, and said imaging region, which are received by said processor.

16. The medical X-ray CT imaging apparatus according to claim 15, wherein
said processor receives a setting whether a subject is a physique of a child or a physique exceeding the physique of the child as said setting of said physique, and
said processor automatically sets at least one setting value defining an output condition corresponding to the physique exceeding the physique of the child and an output condition corresponding to the physique of the child such that a dose based on the output condition corresponding to the physique exceeding the physique of the child is larger than a dose based on the output condition corresponding to the physique of the child.

17. The medical X-ray CT imaging apparatus according to claim 10, wherein said processor automatically sets at least one of a tube voltage of said X-ray generator, a tube current of said X-ray generator, and time during which said X-ray generator emits an X-ray as said output condition of said X-ray generator.

18. The medical X-ray CT imaging apparatus according to claim 10, wherein said processor receives settings of a low dose mode and a high resolution mode, wherein said processor automatically sets said output condition of said X-ray generator according to said setting of said imaging area when said low dose mode is received by said mode setting receiving unit.

19. A medical X-ray CT imaging condition setting method for setting a condition in performing X-ray CT imaging in a medical X-ray CT imaging apparatus including an X-ray generator that generates a cone beam; an X-ray detector; a support that supports said X-ray generator and said X-ray detector while said X-ray generator and said X-ray detector are opposed to each other; and an actuator that turns said X-ray generator and said X-ray detector, which are supported by said support, the medical X-ray CT imaging condition setting method comprising the steps of a processor for:

setting automatically an output condition of said X-ray generator according to at least one of a size of an imaging area, an imaging purpose, and an imaging region, which are input when a setting of said imaging area relating to at least one of said size of said imaging area, said imaging purpose, and said imaging region is input as imaging information;

receiving settings of a first imaging area and a second imaging area wider than said first imaging area as said setting relating to said size of said imaging area, and automatically setting at least one setting value defining a first output condition for a dose based on said first output condition corresponding to said size of said first imaging area, and a second output condition for a dose based on said second output condition corresponding to said size of said second imaging area; and receiving a setting of an imaging area where a boundary circle or a circumscribed circle has a diameter of R1 (mm) as said first imaging area while receiving a setting of an imaging area where a boundary circle or a circumscribed circle has a diameter of R2 (mm) as said second imaging area, where, for a value k1 satisfying 40 (mm)<k1 (mm)<70 (mm), an expression of R1 (mm)<k1 (mm)<R2 (mm) is satisfied.

20. A medical X-ray CT imaging condition setting method for setting a condition in performing X-ray CT imaging in a medical X-ray CT imaging apparatus including an X-ray generator that generates a cone beam; an X-ray detector; a support that supports said X-ray generator and said X-ray detector while said X-ray generator and said X-ray detector are opposed to each other; and an actuator that turns said X-ray generator and said X-ray detector, which are supported by said support, the medical X-ray CT imaging condition setting method comprising the steps of a processor for:

setting automatically an output condition of said X-ray generator according to at least one of a size of an imaging area, an imaging purpose, and an imaging region, which are input when a setting of said imaging area relating to at least one of said size of said imaging area, said imaging purpose, and said imaging region is input as imaging information; receiving settings of a first imaging area and a second imaging area wider than said first imaging area as said setting relating to said size of said imaging area, and automatically setting at least one setting value defining a first output condition for a dose based on said first output condition corresponding to said size of said first imaging area, and a second output condition for a dose based on said second output condition corresponding to said size of said second imaging area; and receiving a setting of an imaging area where a boundary circle or a circumscribed circle has a diameter of R1 (mm) as said first imaging area while receiving a setting of an imaging area where a boundary circle or a circumscribed circle has a diameter of R2 (mm) as said second imaging area, where, for a value k2 satisfying 80 (mm)<k2 (mm)<120 (mm), an expression of R1 (mm)<k2 (mm)<R2 (mm) is satisfied.

21. A non-transitory computer readable medium for a medical X-ray CT imaging condition setting method for setting a condition in performing X-ray CT imaging in a medical X-ray CT imaging apparatus including an X-ray generator that generates a cone beam; an X-ray detector; a support that supports said X-ray generator and said X-ray detector while said X-ray generator and said X-ray detector are opposed to each other; and an actuator that turns said X-ray generator and said X-ray detector, which are supported by said support, the non-transitory computer readable medium having stored thereon an X-ray CT imaging condition setting program configured to, when executed, cause a computer that sets an X-ray CT imaging condition of said medical X-ray CT imaging apparatus to perform the steps of:

setting automatically an output condition of said X-ray generator according to at least one of a size of an imaging area, an imaging purpose, and an imaging region, which are input when a setting of said imaging area relating to at least one of said size of said imaging area, said imaging purpose, and said imaging region is input as imaging information; receiving settings of a first imaging area and a second imaging area wider than said first imaging area as said setting relating to said size of said imaging area, and automatically setting at least one setting value defining a first output condition for a dose based on said first output condition corresponding to said size of said first imaging area and a second output condition for a dose based on said second output condition corresponding to said size of said second imaging area; and receiving a setting of an imaging area where a boundary circle or a circumscribed circle has a diameter of R1 (mm) as said first imaging area while receiving a setting of an imaging area where a boundary circle or a circumscribed circle has a diameter of R2 (mm) as said second imaging area, where, for a value k1 satisfying 40 (mm)<k1 (mm)<70 (mm), an expression of R1 (mm)<k1 (mm)<R2 (mm) is satisfied.

22. A non-transitory computer readable medium for a medical X-ray CT imaging condition setting method for setting a condition in performing X-ray CT imaging in a medical X-ray CT imaging apparatus including an X-ray generator that generates a cone beam; an X-ray detector; a support that supports said X-ray generator and said X-ray detector while said X-ray generator and said X-ray detector are opposed to each other; and an actuator that turns said X-ray generator and said X-ray detector, which are supported by said support, the non-transitory computer readable medium having stored thereon an X-ray CT imaging condition setting program configured to, when executed, cause a computer that sets an X-ray CT imaging condition of said medical X-ray CT imaging apparatus to perform the steps of:

setting automatically an output condition of said X-ray generator according to at least one of a size of an imaging area, an imaging purpose, and an imaging region, which are input when a setting of said imaging area relating to at least one of said size of said imaging area, said imaging purpose, and said imaging region is input as imaging information; receiving settings of a first imaging area and a second imaging area wider than said first imaging area as said setting relating to said size of said imaging area, and automatically setting at least one setting value defining a first output condition for a dose based on said first output condition corresponding to said size of said first imaging area and a second output condition for a dose based on said second output condition corresponding to said size of said second imaging area; and receiving a setting of an imaging area where a boundary circle or a circumscribed circle has a diameter of R1 (mm) as said first imaging area while receiving a setting of an imaging area where a boundary circle or a circumscribed circle has a diameter of R2 (mm) as said second imaging area, where, for a value k2 satisfying 80 (mm)<k2 (mm)<120 (mm), an expression of R1 (mm)<k2 (mm)<R2 (mm) is satisfied.

* * * * *